(12) United States Patent
Hackam

(10) Patent No.: US 9,562,066 B2
(45) Date of Patent: Feb. 7, 2017

(54) ORAL THERAPY OF NECROTIZING ENTEROCOLITIS

(71) Applicant: University of Pittsburgh—of the Commonwealth System of Higher Education, Pittsburgh, PA (US)

(72) Inventor: David J. Hackam, Pittsburgh, PA (US)

(73) Assignee: University of Pittsburgh-Of the Commonwealth System of Higher Education, Pittsburgh, PA (US)

(*) Notice: Subject to any disclaimer, the term of this patent is extended or adjusted under 35 U.S.C. 154(b) by 25 days.

(21) Appl. No.: 14/036,960

(22) Filed: Sep. 25, 2013

(65) Prior Publication Data

US 2014/0086982 A1    Mar. 27, 2014

Related U.S. Application Data

(60) Provisional application No. 61/705,401, filed on Sep. 25, 2012.

(51) Int. Cl.
```
A61K 39/00       (2006.01)
C12N 15/117      (2010.01)
C07H 21/04       (2006.01)
A61K 45/06       (2006.01)
A61K 31/711      (2006.01)
```

(52) U.S. Cl.
CPC ............... *C07H 21/04* (2013.01); *A23L 33/17* (2016.08); *A23L 33/40* (2016.08); *A61K 31/711* (2013.01); *A61K 45/06* (2013.01)

(58) Field of Classification Search
None
See application file for complete search history.

(56) References Cited

U.S. PATENT DOCUMENTS

| | | | |
|---|---|---|---|
| 4,357,322 A | | 11/1982 | Rooks et al. |
| 5,506,204 A | | 4/1996 | Aston |
| 5,756,718 A | | 5/1998 | Christ et al. |
| 5,962,636 A | * | 10/1999 | Bachmaier et al. .......... 530/326 |
| 6,034,230 A | * | 3/2000 | Bachmaier et al. ......... 536/23.5 |
| 6,207,646 B1 | * | 3/2001 | Krieg et al. ................ 514/44 R |
| 6,214,806 B1 | * | 4/2001 | Krieg et al. ................ 514/44 A |
| 6,218,371 B1 | * | 4/2001 | Krieg et al. ................ 514/44 R |
| 6,239,116 B1 | * | 5/2001 | Krieg et al. ................ 514/44 A |
| 6,339,068 B1 | * | 1/2002 | Krieg et al. ................ 514/44 R |
| 6,406,705 B1 | * | 6/2002 | Davis et al. ................ 424/278.1 |
| 6,429,199 B1 | * | 8/2002 | Krieg et al. ................ 514/44 R |
| 6,544,518 B1 | * | 4/2003 | Gerard et al. ............. 424/184.1 |
| 6,558,670 B1 | * | 5/2003 | Friede et al. ............. 424/184.1 |
| 6,613,751 B2 | | 9/2003 | Raz et al. |
| 6,652,392 B2 | * | 11/2003 | Higuchi et al. ............... 473/374 |
| 7,038,029 B2 | | 5/2006 | Lopez |
| 7,049,302 B1 | | 5/2006 | Kensil |
| 7,129,222 B2 | | 10/2006 | Van Nest et al. |
| 7,183,111 B2 | | 2/2007 | Van Nest et al. |
| 7,250,397 B2 | | 7/2007 | Larsen et al. |
| 7,348,316 B2 | | 3/2008 | Rossignol et al. |
| 7,744,884 B2 | | 6/2010 | Elson |
| 7,851,451 B2 | * | 12/2010 | Clandinin et al. ............... 514/25 |
| 8,188,058 B2 | * | 5/2012 | Hackam et al. ............ 514/44 R |
| 8,518,903 B2 | * | 8/2013 | Hackam ...................... 514/44 R |
| 8,518,905 B2 | * | 8/2013 | Hackam et al. ............ 514/44 R |
| 9,072,760 B2 | * | 7/2015 | Wipf .................. A61K 31/7008 |
| 2002/0064515 A1 | * | 5/2002 | Krieg et al. .................. 424/85.1 |
| 2005/0250726 A1 | * | 11/2005 | Krieg et al. .................... 514/44 |
| 2006/0211752 A1 | | 9/2006 | Kohn et al. |
| 2006/0241040 A1 | | 10/2006 | Visintin et al. |
| 2007/0004654 A1 | | 1/2007 | Raz et al. |
| 2008/0311112 A1 | * | 12/2008 | Hackam et al. ............ 424/130.1 |
| 2009/0010902 A1 | | 1/2009 | Masuda |
| 2012/0077868 A1 | * | 3/2012 | Hackam ...................... 514/44 R |
| 2013/0072547 A1 | * | 3/2013 | Hackam et al. ............ 514/44 R |
| 2013/0281395 A1 | | 10/2013 | Wipf et al. |
| 2013/0345154 A1 | | 12/2013 | Hackam |
| 2014/0086982 A1 | * | 3/2014 | Hackam ........................ 424/450 |
| 2014/0377238 A1 | * | 12/2014 | Budelli et al. ............. 424/93.45 |
| 2015/0056217 A1 | * | 2/2015 | Hackam ............... A61K 31/675 424/172.1 |

FOREIGN PATENT DOCUMENTS

| | | |
|---|---|---|
| JP | 01-180894 | 7/1989 |
| WO | WO 98/18810 A1 * | 5/1998 |
| WO | WO 98/37919 A1 * | 9/1998 |
| WO | WO 98/52581 A1 * | 11/1998 |
| WO | WO 99/33488 A2 * | 7/1999 |
| WO | WO 98/58118 A2 * | 11/1999 |

(Continued)

OTHER PUBLICATIONS

Fukata et al, Biochemical Society Transactions, 2007, 35/6:1473-1478.*
Sodhi et al, Gastroenterology, 2010, 138:185-196.*
Anand et al, SHOCK, 2007, 27/2:124-133.*
Gribar et al, Journal of Immunology, 2009, 182:636-646.*
Arciero et al, Journal of Theoretical Biology, 2013, 321:83-99.*
Abreu, Nature Reviews|Immunology, Feb. 2010, 10:131-143.*
Sartor, Current Opinion in Gastroenterology 2003, 19:358-365.*
U.S. Appl. No. 14/010,232, filed Aug. 26, 2013.
U.S. Appl. No. 12/104,816, May 14, 2013 Certificate of Correction.
U.S. Appl. No. 12/104,816, Apr. 23, 2012 Issue Fee payment.
U.S. Appl. No. 12/104,816, Jan. 23, 2012 Notice of Allowance.
U.S. Appl. No. 12/104,816, Nov. 10, 2011 Amendment and Request for Continued Examination (RCE).
U.S. Appl. No. 12/104,816, May 10, 2011 Final Office Action.
U.S. Appl. No. 12/104,816, Feb. 24, 2011 Response to Non-Final Office Action.

(Continued)

*Primary Examiner* — Nita M Minnifield
(74) *Attorney, Agent, or Firm* — Baker Botts, LLP

(57) ABSTRACT

The present invention relates to methods of treating or reducing the risk of necrotizing enterocolitis (NEC) in an infant comprising orally administering an effective amount of a CpG-ODN. It is based, at least in part, on the results of experiments in which orally administered CpG-ODNs were observed to reduce the histopathology and markers of inflammation in a murine model for NEC. The present invention further provides for oral formulations of CpG-ODN for administration to infants.

6 Claims, 9 Drawing Sheets

(56) References Cited

FOREIGN PATENT DOCUMENTS

Figure 1:
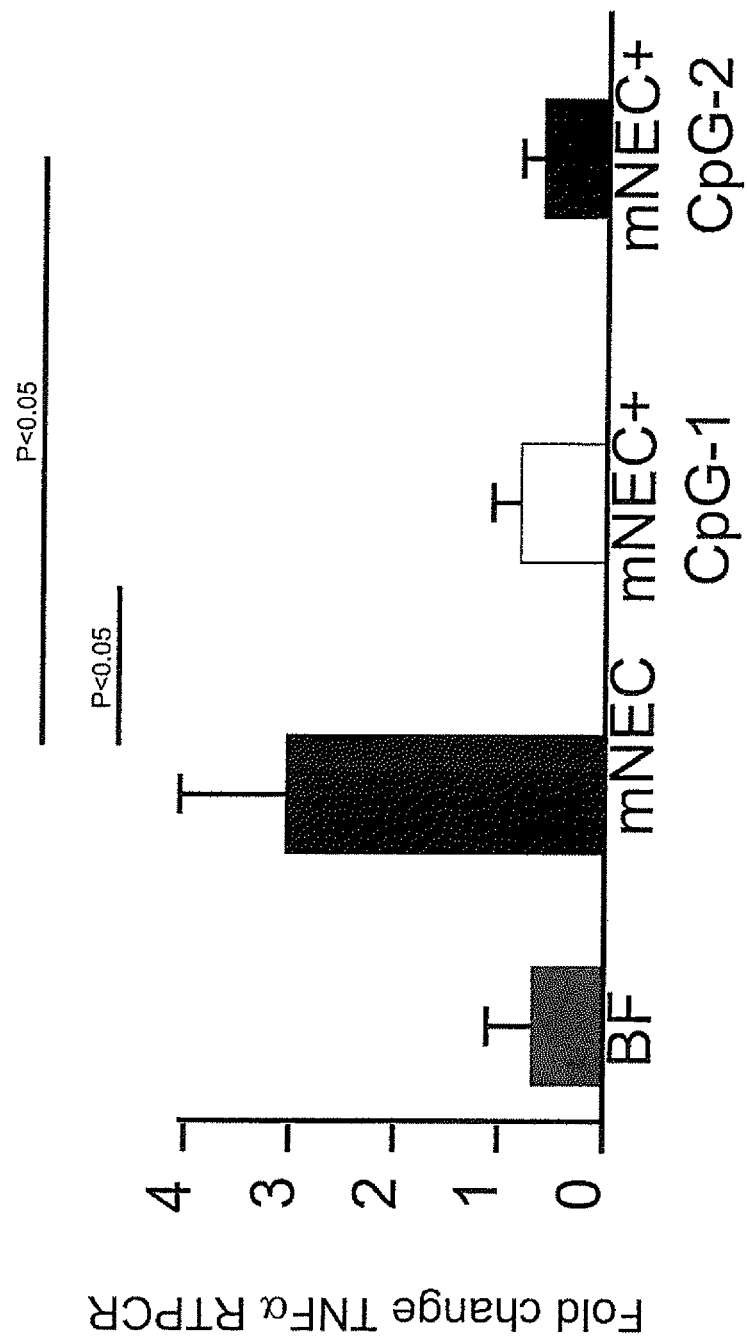

| WO | WO 00/61555 | 10/2000 |
|---|---|---|
| WO | WO 2004/096156 | 11/2004 |
| WO | WO 2006/092049 | 9/2006 |
| WO | WO 2007/106886 | 9/2007 |
| WO | WO 2007/120368 | 10/2007 |
| WO | WO 2008/131074 A1 * | 10/2008 |
| WO | WO 2014/052453 A1 * | 4/2014 |

OTHER PUBLICATIONS

U.S. Appl. No. 12/104,816, Nov. 24, 2010 Non-Final Office Action.
U.S. Appl. No. 12/104,816, Sep. 15, 2010 Response to Restriction Requirement.
U.S. Appl. No. 12/104,816, Aug. 9, 2010 Restriction Requirement.
U.S. Appl. No. 13/068,553, Jul. 25, 2013 Issue Fee payment.
U.S. Appl. No. 13/068,553, Apr. 30, 2013 Notice of Allowance.
U.S. Appl. No. 13/068,553, Apr. 12, 2013 Response to Non-Final Office Action.
U.S. Appl. No. 13/068,553, Jan. 15, 2013 Non-Final Office Action.
U.S. Appl. No. 13/461,672, Jul. 25, 2013 Issue Fee payment.
U.S. Appl. No. 13/461,672, Apr. 29, 2013 Notice of Allowance.
U.S. Appl. No. 13/461,672, Apr. 12, 2013 Response to Non-Final Office Action.
U.S. Appl. No. 13/461,672, Jan. 14, 2013 Non-Final Office Action.
U.S. Appl. No. 13/921,865, Mar. 11, 2015 Final Office Action.
U.S. Appl. No. 13/921,865, Nov. 14, 2014 Response to Non-Final Office Action.
U.S. Appl. No. 13/921,865, Aug. 14, 2014 Non-Final Office Action.
U.S. Appl. No. 13/921,865, Jul. 10, 2014 Response to Non-Final Office Action.
U.S. Appl. No. 13/921,865, Mar. 12, 2014 Non-Final Office Action.
U.S. Appl. No. 13/921,865, Nov. 27, 2013 Response to Restriction Requirement.
U.S. Appl. No. 13/921,865, Sep. 27, 2013 Restriction Requirement.
U.S. Appl. No. 13/848,809, Nov. 10, 2014 Notice of Allowance.
U.S. Appl. No. 13/848,809, Feb. 3, 2015 Request for Continued Examination (RCE).
U.S. Appl. No. 13/848,809, Feb. 17, 2015 Notice of Allowance.
U.S. Appl. No. 13/848,809, May 12, 2015 Issue Fee Payment.
U.S. Appl. No. 14/010,232, Jun. 19, 2015 Non-Final Office Action.
International Search Report for PCT/US2011/053293, dated Apr. 9, 2012.
Abreu et al., 2005, "TLR Signaling in the Gut in Health and Disease." J Immunol 174:4453-4460.
Achkar, "Ulcerative colitis: Responding to the challenges", *Cleveland Clinic J. Med.*, 2007; 74(9):657-660.
Afrazi et al. "New insights into the pathogenesis and treatment of necrotizing enterocolitis: Toll-like receptors and beyond", *Pediatr Res.*, 2011; 69:183-188.
Afrazi et al., "Intracellular heat shock protein-70 negatively regulates TLR4 signaling in the newborn intestinal epithelium", *J. Immunol.*, 2012, 188:4543-4557.
Aki Tsukioka, "Eisai Successfully Completes Phase II Trial of Eritoran, Drug Candidate for Severe Sepsis." JCN Network, Aug. 30, 2005 p. 1. Downloaded on Nov. 20, 2009 from http://www.japancorp.net/printarticle.asp?Art_ID=10765.
Amer et al., "Platelet-activating factor concentration in the stool of human newborns: effects of enteral feeding and neonatal necrotizing enterocolitis", *Biol Neonate*, 2004; 85:159-166.
Anand et al., 2007, "The Role of the Intestinal Barrier in the Pathogenesis of Necrotizing Enterocolitis." Shock 27:124-133.
Anderson, 2001, "Infant, neonatal, and postnatal deaths, percent of total deaths, and mortality rates for the 10 leading causes of infant death by race and sex: United States: 1999." National Vital Statistics Reports. 49:73.
Blakely et al., "Postoperative outcomes of extremely low birth-weight infants with necrotizing enterocolitis or isolated intestinal perforation: a prospective cohort study by the NICHD Neonatal Research Network", *Ann Surg.* 2005; 241(6):984-989.
Borges et al., "Immune response by nasal delivery of hepatitis B surface and antigen and codelivery of a CpG ODN in alginate coated chitosan nanoparticles", *European Journal of Pharmaceutics and Biopharmaceutics*, 59:405-416 (2008).
Borzutzky et al., "NOD2-associated diseases: Bridging innate immunity and autoinflammation", *Clin Immunol.*, 2010; 134:251-261.
Caplan et al., "The platelet activating factor receptor antagonist WEB 2170 prevents neonatal necrotizing enterocolitis in rats", *J Pediatr Gastroenterol Nutr.* 1997; 24:296-301.
Caplan et al., "The role of recombinant platelet activating factor acetylhydrolase in a neonatal rat model of necrotizing enterocolitis", *Pediatr Res.*, 1997; 42:779-783.
Caplan et al., "Neonatal necrotizing enterocolitis: possible role of probiotic supplementation", *Journal of Pediatric Gastroenterology and Nutrition*, 30(2):S18-S22 (2000).
Caradonna et al., "Phagocytosis, killing, lymphocyte-mediated antibacterial activity, serum autoantibodies, and plasma endotoxins in inflammatory bowel disease", *Am J Gastroenterol.* 2000; 95:1495-1502.
Career Opportunities—Eisai announces Phase II results, plans to initiate phase III clinical—Aug. 29, 2005. Downloaded on Apr. 18, 2007 from http://www.eisai.com/view_pressrelease.asp?ID=145&press=124.
Cario et al., 2000, "Lipopolysaccharide activates distinct signaling pathways in intestinal epithelial cell lines expressing Toll-like receptors." J Immunol. 164(2):966-72.
Carneiro et al., 2008, "Nod-like proteins in inflammation and disease." J Pathol. 214(2):136-48.
Cavallo et al., 2006 "The expression and function of enterocyte toll like receptor-4 are enhanced by lipopolysaccharide in vitro and during systemic endotoxemia." Association for academic surgery and society of university surgeons—Abstracts. Journal of Surgical Research vol. 130, Issue 2, p. 232, No. 189.
Cetin et al., 2004, "Endotoxin inhibits intestinal epithelial restitution through activation of Rho-GTPase and increased focal adhesions." J Biol Chem. 279(23):24592-600. Epub Mar. 30, 2004.
Cetin et al., 2007, "Nitric oxide inhibits enterocyte migration through activation of RhoA-GTPase in a SHP-2-dependent manner." Am J Physiol Gastrointest Liver Physiol 292:G1347-1358.
Chan et al., "Role of LPS/CD14/TLR4-mediated inflammation in necrotizing enterocolitis: pathogenesis and therapeutic implications", *World J Gastroenterol.*, 2009; 15:4745-4752.
Cho et al., 2007, "The genetics of inflammatory bowel disease." Gastroenterology 133:1327-1339.
Creagh et al., 2006, "TLRs, NLRs and RLRs: a trinity of pathogen sensors that co-operate in innate immunity." Trends Immunol. 27(8):352-7. Epub Jun. 27, 2006.
Dai et al., "Extracellular high mobility group box1 (HMGB1) inhibits enterocyte migration via activation of toll like receptor 4 and increased cell-matrix adhesiveness", *J Biol Chem.*, 2010; 285:4995-5002.
Daubenberger, 2007, "TLR9 agonists as adjuvants for prophylactic and therapeutic vaccines." Curr. Opin. Molec. Ther. 9:45-52.
Ding et al., 1998, "Characterization and quantitation of NF-kappaB nuclear translocation induced by interleukin-1 and tumor necrosis factor-alpha. Development and use of a high capacity fluorescence cytometric system." J Biol Chem. 273(44):28897-905.
Diwan et al., "Enhancement of immune responses by co-delivery of a CpG oligodeoxynucleotide and tetanus toxoid in biodegradable nanospheres", *J. Control Release*, 85(1-3):247-262 (2002).
Duffy et al., "Concordance of bacterial cultures with endotoxin and interleukin-6 in necrotizing enterocolitis", *Dig Dis Sci.* 1997; 42:359-365.
Ewaschuk et al., 2007, "Surface expression of Toll-like receptor 9 is upregulated on intestinal epithelial cells in response to pathogenic bacterial DNA." Infect Immun. 75(5):2572-9. Epub Feb. 26, 2007.
Ey et al., "TLR2 mediates gap junctional intercellular communication through connexin-43 in intestinal epithelial barrier injury", *The Journal of Biological Chemistry*, 284:22332-22343 (2009).

(56) References Cited

OTHER PUBLICATIONS

Feng et al., "Heparin-binding epidermal growth factor-like growth factor promotes enterocyte migration and proliferation in neonatal rats with necrotizing enterocolitis", *J Pediatr Surg.*, 2007; 42:214-220.
Feng et al., 2005, "Heparin-binding EGF-like growth factor (HB-EGF) and necrotizing enterocolitis." Semin Pediatr Surg. 14(3):167-74.
Franchi et al., 2008, "Intracellular NOD-like receptors in innate immunity, infection and disease." Cell Microbiol 10:1-8.
Fukata et al., "Cox-2 is regulated by Toll-like receptor-4 (TLR4) signaling: Role in proliferation and apoptosis in the intestine", *Gastroenterology*, 2006; 131:862-877.
Fukata et al., "Toll-like receptor-4 is required for intestinal response to epithelial injury and limiting bacterial translocation in a murine model of acute colitis", *Am J Physiol Gastrointest Liver Physiol.*, 2005; 288:G1055-G1065.
Fukata et al., "Innate immune signaling by Toll-like receptor-4 (TLR4) shapes the inflammatory microenvironment in colitis-associated tumors", *Inflamm Bowel Dis.* 2009; 15 :997-1006.
Fukata et al., "TLR4 signaling in the intestine in health and disease", *Biochemical Society Transactions*, 35(6):1473-1478 (2007).
Gagliardi et al., "Necrotising enterocolitis in very low birth weight infants in Italy: incidence and non-nutritional risk factors", *J. Pediatr Gastroenterol Nutr.*, 2008; 47(2):206-210.
Good, et al., "Evidence based feeding strategies before and after the development of necrotizing enterocolitis", *Expert Rev Clin Immunol.*, Jul. 2014: 10(7):875-884.
Goodenough, "Bulk isolation of mouse hepatocyte gap junctions. Characterization of the principal protein connexin", *J. Cell Biol.*, 1974; 61: 557-563.
Goodenough, "The structure of cell membranes involved in intercellular communication", *Am. J. Clin. Pathol.*, 1975; 63:636-645.
Grave et al., "New therapies and preventive approaches for necrotizing enterocolitis: report of a research planning workshop", *Pediatr Res.*, 2007; 62:510-514.
Gribar et al., "Reciprocal expression and signaling of TLR4 and TLR9 in the pathogenesis and treatment of necrotizing enterocolitis", *Journal of Immunologists*, 182(1):636-646 (2009).
Gribar et al., 2008, "The role of epithelial Toll-like receptor signaling in the pathogenesis of intestinal inflammation." J Leukoc Biol. 83(3):493-8. Epub Dec. 26, 2007.
Grimm et al., "NOD2 Mutations and Crohn's Disease: Are Paneth Cells and Their Antimicrobial Peptides the Link?" Gut; 53(11): 1558-1560, Nov. 2004, entire document especially p. 2.
Guthrie et al., 2003, "Necrotizing enterocolitis among neonates in the United States." J Perinatol 23:278-285.
Hackam et al., "Mechanisms of gut barrier failure in the pathogenesis of necrotizing enetrocolitis: toll like receptors throw the switch", *Semin Pediatr Surg* 22(2):76-82, May 2013.
Halpern et al., "Reduction of experimental necrotizing enterocolitis with anti-TNF-alpha", Am J Physiol Gastrointest Liver Physiol 290:757-764, 2006, First published Nov. 3, 2005, entire document especially abstract; p. 1.
Halpern et al., 2006, "Reduction of experimental necrotizing enterocolitis with anti-TNF-α." Am J. Physiol Gastrointest Liver Physiol 290, pp. G757-G764.
Henckaerts et al., "NOD/CARD 15 disease associations other than Crohn's disease", *Inflamm Bowel Dis* 13(2):235-241, 2007.
Henry et al., 2006, "Laparotomy Versus Peritoneal Drainage for Perforated Necrotizing Enterocolitis." Neoreviews 7:456-462.
Henry et al., 2005, "Surgical therapy for necrotizing enterocolitis: bringing evidence to the bedside." Semin Pediatr Surg. 14(3):181-90.
Hotta et al., "Lipopolysaccharide-induced colitis in rabbits", *Res Exp Med (Berl)* 1986; 186:61-69.
Hsueh et al., 2003, "Neonatal necrotizing enterocolitis: clinical considerations and pathogenetic concepts." Pediatr Dev Pathol 6:6-23.

Hugot et al., "Association of NOD2 leucine-rich repeat variants with susceptibility to Crohn's disease." Nature. 411(6837):599-603 (2001).
InvivoGen: Delivering Genes. "TLR9 Ligands." Downloaded on Apr. 16, 2007 from hrrp://www.invivogen.com/family.php?ID=104 &ID_cat=2&ID_sscat=9.
Iwasaki et al., "Regulation of adaptive immunity by the innate immune system", *Science*, 2010; 327:291-295.
Izumi et al., "Platelet-activating factor receptor: gene expression and signal transduction", *Biochim Biophys Acta*, 1995; 1259:317-333.
Jesse et al., 2006, "Necotrizing enterocolitis: Relationship to Innate Immunity, Clinical Features, and Strategies for Prevention." NeoReviews 7:143-150.
Jilling et al., "The roles of bacteria and TLR4 in rat and murine models of necrotizing enterocolitis." J Immunol. 177(5):3273-82 (2006).
Kanneganti et al., 2007, "Intracellular NOD-like receptors in host defense and disease." Immunity 27:549-559.
Katakura et al., "Toll-like receptor 9-induced type I IFN protects mice from experimental colitis." J Clin Invest. 115(3):695-702. Erratum in: J Clin Invest. 2005 115(4):1100 (2005).
Kitagaki et al., "Oral administration of CpG-ODNs suppresses antigen-induced asthma in mice", *British Society for Immunology, Clinical and Experimental Immunology*, 143:249-259 (2005).
Knapp, et al., "Thionation: GlcNAc-Thiazoline Triacetate {(3aR,5R,6S,7R,7aR)-5-Acetoxymethyl-6, 7-Diacetoxy-2-Methyl-5,6,7,7a-Tetrahydro-3aH-Pyrano[3,2-d]Thiazole}", *Organic Syntheses*, 84:68-76 (2007).
Kobayashi et al., "Suppression of murine endotoxin response by E5531, a novel synthetic lipid A antagonist." Antimicrob Agents Chemother. 42(11):2824-9 (1998).
Kosloske, 1994, "Epidemiology of necrotizing enterocolitis." Acta Pediatr. Suppl. 396:2-7.
Krieg, 2006, "Therapeutic potential of Toll-like receptor 9 activation." Nat. Rev. Drug Disc. 5:471-484.
Kruis et al., "Circulating lipid A antibodies despite absence of systemic endotoxemia in patients with Crohn's disease", *Dig Dis Sci.*, 1984; 29:502-507.
Laird, "Connexin phosphorylation as a regulatory event linked to gap junction internalization and degradation", *Biochi. Biophys. Acta*, 2005; 1711: 172-182.
Lampe et al., "Phosphorylation of connexin-43 on serine 368 by protein kinase C regulates gap junction communication", *J. Cell Biol.*, (2000) 149:1503-1512.
Lavelle et al., "The role of TLRs, NLRs, and RLRs in mucosal innate immunity and homeostasis", *Mucosal Immunol* 3(1):17-28, online Nov. 4, 2009.
Lee et al., 2006, "Homeostatic effects of TLR9 signaling in experimental colitis." Ann N Y Acad Sci. 1072:351-5.
Leapart et al., "Interferon-γ inhibits enterocyte migration by reversibly displacing connexion43 from lipid rafts", *Am J Physiol Gastrointest Liver Physiol*, 2008; 295:G559-G569.
Leaphart et al., 2007. "A Critical Role for TLR4 in the Pathogenesis of Necrotizing Enterocolitis by Modulating Intestinal Injury and Repair." J Immunology 179:4808-4820.
Leaphart et al., 2007, "Interferon-gamma inhibits intestinal restitution by preventing gap junction communication between enterocytes." Gastroenterology. 132(7):2395-411. Epub Mar. 21, 2007.
Lemaitre et al., "The dorsoventral regulatory gene cassette spätzle/Toll/cactus controls the potent antifungal response in *Drosophila* adults", *Cell*, 1996; 86:973-983.
Lin et al., "Oral probiotics reduce the incidence and severity of necrotizing enterocolitis in very low birth weight infants", *Pediatrics*, 2005; 115:1-4.
Lin et al., 2006, "Necrotising enterocolitis." Lancet 368:1271-1283.
Liu et al., "Changes in intestinal toll-like receptors and cytokines precede histological injury in a rat model of necrotizing enterocolitis", *Am J Physiol Gastrointest Liver Physiol.*, 2009; 297:G442-G450.
Lotz et al., "Postnatal acquisition of endotoxin tolerance in intestinal epithelial cells", *J Exp Med.*, 2006; 203:973-984.

(56) References Cited

OTHER PUBLICATIONS

Lu et al., "Polyunsaturated fatty acid supplementation alters proinflammatory gene expression and reduces the incidence of necrotizing enterocolitis in a neonatal rat model", *Pediatr Res.*, 2007; 61:427-432.
Luig et al., "Epidemiology of necrotizing enterocolitis—PartI: Changing regional trends in extremely preterm infants over 14 years", *J. Paediatr Child Health*, 2005; 41(4):169-73.
Macagno et al., 2006, "A cyanobacterial LPS antagonist prevents endotoxin shock and blocks sustained TLR4 stimulation required for cytokine expression." J. Exp. Med. 203(6):1481-1492.
Maeda et al., 2005, "Nod2 mutation in Crohn's disease potentiates NF-kappaB activity and IL-1beta processing." Science 307:734-738. Erratum in Science. Apr. 29, 2005;308(5722):633.
Medzhitov et al., "A human homologue of the *Drosophila* Toll protein signals activation of adaptive immunity", *Nature*, 1997; 388:394-397.
Merck Manual website, Nov. 2007 by William J. Cochran, MD. Downloaded on Nov. 7, 2011 from <http://www.merckmanuals.com/professional/pediatrics/gastrointestinal_disorders_in_neonates_and_infants/necrotizing_enterocolitis.html>.
Michaelsson et al., "Regulation of T cell responses in the developing human fetus", *J. Immunol.*, 2006; 176(10):5741-5748.
Milla et al., "Small intestinal motility patterns in the perinatal period", *J Pediatr. Gastroenterol Nutr.*, 1983; 2:S141-S144.
Mizrahi et al., "Necrotizing enterocolitis in premature infants", *J Pediatr.*, 1965; 66:697-705.
Moss et al., 2006, "Laparotomy versus peritoneal drainage for necrotizing enterocolitis and perforation." N. Engl. J. Med. 354:2225-2234.
Muguruma et al., "The central role of PAF in necrotizing enterocolitis development", *Adv Exp Med Biol.* 1997; 407:379-382.
Mullarkey et al., 2003, "Inhibition of endotoxin response by e5564, a novel Toll-like receptor 4-directed endotoxin antagonist." J Pharmacol Exp Ther. 304(3):1093-102.
Neal et al., "A critical role for TLR4 induction of autophagy in the regulation of enterocyte migration and the pathogenesis of necrotizing enterocolitis", *J. Immunol.*, 2013; 190(7):3541-3551.
Neal et al., "Enterocyte TLR4 mediates phagocytosis and translocation of bacteria across the intestinal barrier." J Immunol. 176(5):3070-9 (2006).
Neu et al., 2005, "Intestinal innate immunity: how does it relate to the pathogenesis of necrotizing enterocolitis." Semin. Pediatr. Surg. 14: 137-144.
Neu, 1996, "Necrotizing enterocolitis: the search for a unifying pathogenic theory leading to prevention." Pediatr Clin North Am. 43(2):409-32.
Ng, 2001, "Necrotizing enterocolitis in the full-term neonate." J Paediatr Child Health. 37(1):1-4.
Noerr, "Current controversies in the understanding of necrotizing enterocolitis", *Adv Neonatal Care*, 2003; 3:107-120.
Obermeier et al., "Contrasting activity of cytosin-guanosin dinucleotide oligonucleotides in mice with experimental colitis", *Clin Exp Immunol.*, 134(2):217-224 (2003).
Obermeier et al. 2002, "CpG motifs of bacterial DNA exacerbate colitis of dextran sulfate sodium-treated mice." Eur J Immunol. Jul. 2002;32(7):2084-92.
Ogura et al., "A frameshift mutation in NOD2 associated with susceptibility to Crohn's disease." Nature. 411(6837):603-6 (2001).
Otte et al., 2004, "Mechanisms of cross hyporesponsiveness to Toll-like receptor bacterial ligands in intestinal epithelial cells." Gastroenterology. 126(4):1054-70.
Panigrahi, "Necrotizing enterocolitis", *Paediatr. Drugs*, 2006; 8(3):151-165.
Parant et al., "Stimulation of non-specific resistance to infections by synthetic immunoregulatory agents", *Infection* 12(3):230-234, 1984.
Pierro, 2005, "The surgical management of necrotising enterocolitis." Early Hum Dev. 81(1):79-85.
Poltorak et al., 1998, "Defective LPS Signaling in C3H/HeJ and C57BL/10ScCr Mice: Mutations in Tlr4 Gene." Science 282: 2085-2088.
Prohinar et al., "Specific high affinity interactions of monomeric endotoxin.protein complexes with Toll-like receptor 4 ectodomain." J Biol Chem. 282(2):1010-7. (2007).
Putta et al., 2006, "Novel oligodeoxynucleotide agonists of TLR9 containing N3-Me-dC or N1-Me-dG modifications." Nucleic Acids Res. 34(11):3231-8.
Qureshi et al., "Increased expression and function of integrins in enterocytes by endotoxin impairs epithelial restitution", *Gastroenterology*, 2005; 128:1012-1022.
Rachmelewitz et al., 2004, "Toll-like receptor 9 signaling mediates the anti-inflammatory effects of probiotics in murine experimental colitis." Gastroenterology. 126(2):520-8.
Rakoff-Nahoum et al., "Recognition of commensal microflora by toll-like receptors is required for intestinal homeostasis", *Cell*, 2004; 118:229-241.
Richardson, et al., "Nucleotide-binding Oligomerization Domain-2 Inhibits Toll Like Receptor-4 Signaling in the Intestinal Epithelium", *Gastroenterology*, 139(3):904-917 (2010).
Roach et al., "The evolution of vertebrate Toll-like receptors", *PNAS*, 2005; 102:9577-9582.
Rossignol et al., 2004, "Safety, pharmacokinetics, pharmacodynamics, and plasma lipoprotein distribution of eritoran (E5564) during continuous intravenous infusion into healthy volunteers." Antimicrob Agents Chemother. 48(9):3233-40.
Sodhi, et al., "DNA Attenuates Enterocyte Toll-like Receptor 4-Mediated Intestinal Mucosal Injury After Remote Trauma", *Am J Physiol Gastrointest Liver Physiol.*, 300:G862-G873 (2011).
Sodhi, et al., "Toll-like-receptor-4 Inhibits Enterocyte Proliferation via Impaired β-Catenin Signaling in Necrotizing Enterocolitis", *Gastroenterology*, 138(1):185-196 (2010).
Shan et al., "Regulation of toll-like receptor 4-induced proasthmatic changes in airway smooth muscle function by opposing actions of ERK1/2 and p38 MAPK signaling", *Am J. Physiol. Lung Cell Mol. Physiol.*, 291(3):L324-L333 (2006).
Sharma et al., 2007, "Neonatal gut barrier and multiple organ failure: role of endotoxin and proinflammatory cytokines in sepsis and necrotizing enterocolitis." J Pediatr Surg 42:454-461.
Shin et al., 2000, "Diminished epidermal growth factor levels in infants with necrotizing enterocolitis." J Pediatr Surg. 35(2):173-6; discussion 177.
Shindou et al., "Roles of cytosolic phospholipase A2 and platelet-activating factor receptor in the Ca-induced biosynthesis of PAF", *Biochem Biophys Res Commun.* 2000; 271:812-817.
Shuto et al., "Activation of NF-kappa B by nontypeable hemophilus influenzae is mediated by toll-like receptor 2-TAK1-dependent NIK-IKK alpha/beta-I kappa B alpha and MKK3/6-p38 MAP kinase signaling pathways in epithelial cells", *PNAS*, 98(15):8774-8779 (2001).
Strober et al., 2006, "Signalling pathways and molecular interactions of NOD1 and NOD2." Nat Rev Immunol. 6:9-20.
Supplemental European Search Report for EP Application No. 08746070.5, dated May 25, 2011.
Svetlov et al., "Regulation of platelet-activating factor (PAF) biosynthesis via coenzyme A-independent transacylase in the macrophage cell line IC-21 stimulated with lipopolysaccharide", *Biochim Biophys Acta*, 1997; 1346:120-130.
Takeda et al., "Toll-like receptors in innate immunity." Int Immunol. 17(1):1-14.
Takeda et al., 2001, "Roles of Toll-like receptors in innate immune responses." Genes Cells 6:733-742.
Tatum et al., "The role of toll-like receptor 9 in an animal model of necrotizing enterocolitis", *Journal of Investigative Medicine*, 58(2):436 (2010).
Thompson et al., "Necrotizing enterocolitis in newborns", *Drugs*, 2008; 68(9):1227-1238.
Wolfs et al., "Localization of the lipopolysaccharide recognition complex in the human healthy and inflamed premature and adult gut", *Inflamm Bowel Dis.*, 2010; 16:68-75.
Uauy et al., 1991, "Necrotizing enterocolitis in very low birth weight infants: biodemographic and clinical correlates." National

(56) References Cited

OTHER PUBLICATIONS

Institute of Child Health and Human Development Neonatal Research Network. J Pediatr 119:630-638.
University of Pittsburgh Department of Critical Care Medicine: Research—The Crisma Laboratory, pp. 1-11. Downloaded on Apr. 19, 2007 from http:/www.ccm.upmc.edu/research/res_crisma.htlm.
Van Heel et al., "Synergy between TLR9 and NOD2 innate immune responses is lost in genetic Chrohn's disease" *GUT, British Medical Association*, 54(11):1553-1557 (2005).
Verma et al., "Novel pharmacophores of connexin-43 based on the "RXP" series of Cx43-binding peptides", *Circ. Res.*, 2009; 105(2):176-184.
Verthelyi et al., "Human peripheral blood cells differentially recognize and respond to two distinct CPG motifs." J Immunol. 166(4):2372-7 (2001).
Vink et al., 2002, "In vivo evidence for a role of toll-like receptor 4 in the development of intimal lesions." Circulation. 106(15):1985-90.
Wang et al., "NF-κB-mediated expression of MAPK phosphatase-1 is an early step in desensitization to TLR ligands in enterocytes", *Mucosal Immunol.*, 2010; 3:523-534.
Wang et al., "Ubiquitin-editing enzyme A20 promotes tolerance to lipopolysaccharide in enterocytes", *J Immunol.*, 2009; 183:1384-1392.
Warner et al., 2005, "Role of epidermal growth factor in the pathogenesis of neonatal necrotizing enterocolitis." Semin Pediatr Surg. 14(3):175-80.
Watanabe et al., "Muramyl dipeptide activation of nucleotide-binding oligomerization domain 2 protects mice from experimental colitis." J Clin Invest 118:545-559 (2008).
Wirtz et al., "Illuminating the role of type I IFNs in colitis." J Clin Invest. 115(3):586-8 (2005).
Worthen et al., "The priming of neutrophils by lipopolysaccharide for production of intracellular platelet-activating factor: potential role in mediation of enhanced superoxide secretion", *J Immunol.*, 1988; 140:3553-3559.
Wynn et al., "The host response to sepsis and developmental impact", *Pediatrics*, 2010; 125:1031-1041.
Yang et al., "NOD2 transgenic mice exhibit enhanced MDP-mediated down-regulation of TLR2 responses and resistance to colitis induction." Gastroenterology 133:1510-1521 (2007).
Yang et al., 2005, "Role of Toll-like receptor 4/NF-kappaB pathway in monocyte-endothelial adhesion induced by low shear stress and ox-LDL." Biorheology. 42(3):225-36.
Yang et al., 2007, "NOD2 pathway activation by MDP or *Mycobacterium tuberculosis* infection involves the stable polyubiquitination of Rip2." J Biol Chem 282:36223-36229.
Zhai et al., "Cutting edge: TLR4 activation mediates liver ischemia/reperfusion inflammatory response via IFN regulatory factor 3-dependent MyD88-independent pathway", *J. Immunol.*, 173(12):7115-7119 (2004).
Zheng et al., "Regulation of colonic epithelial repair in mice by Toll-like receptors and hyaluronic acid", *Gastroenterology*, 2009; 137:2041-2051.
Zhou et al., "Oral administration of plant-based rotavirus VP6 induces antigen-specific IgAs, IgGs and passive protection in mice" *Vaccine*, 28:6021-6027 (2010).
Zouali et al., "CARD15/NOD2 is not a predisposing factor for necrotizing enterocolitis", *Digestive Diseases and Sci* 50(9):1684-1687, 2005.
U.S. Appl. No. 13/921,865, Aug. 8, 2016 Final Office Action.
U.S. Appl. No. 13/921,865, Apr. 25, 2016 Response to Non-Final Office Action.
U.S. Appl. No. 13/921,865, Jan. 25, 2016 Non-Final Office Action.
U.S. Appl. No. 13/921,865, Aug. 11, 2015 Amendment and Request for Continued Examination (RCE).
U.S. Appl. No. 14/010,232, Aug. 10, 2016 Amendment and Request for Continued Examination (RCE).
U.S. Appl. No. 14/010,232, May 10, 2016 Final Office Action.
U.S. Appl. No. 14/010,232, Sep. 21, 2015 Response to Non-Final Office Action.
IEC-6 cells, Sigma Aldrich, accessed Aug. 2, 2016 at URL sigmaaldrich.com/catalog/product/sigma/88071401, 1 page.

\* cited by examiner

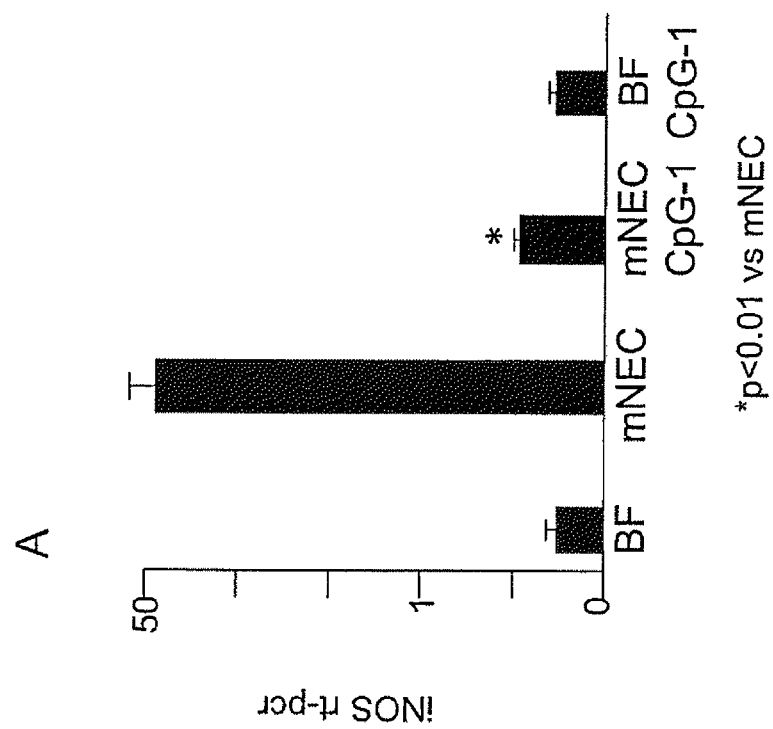
Figure 6A-B

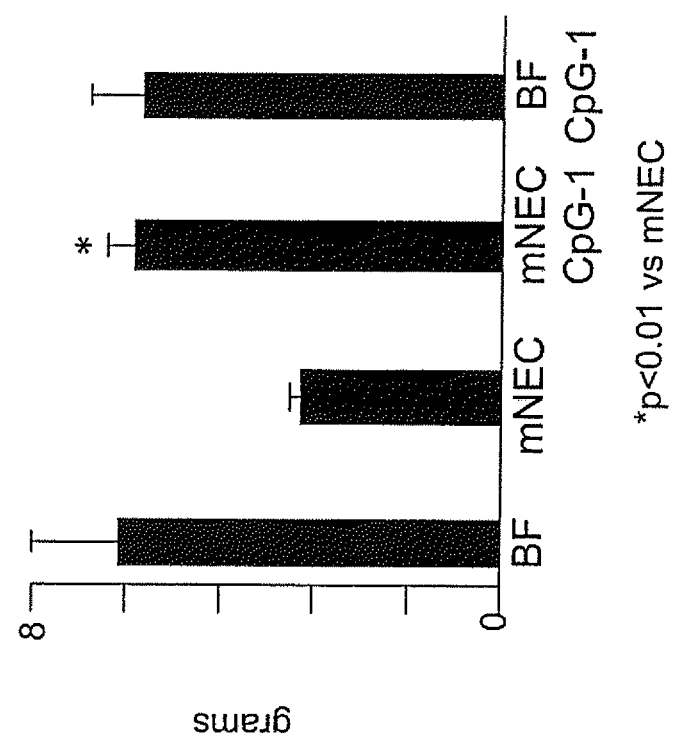

CpG inhibits TLR4-mediated inflammation in human ex vivo Control and NEC intestinal tissue Each sample divided into 12 pieces, one patient per group

ORAL THERAPY OF NECROTIZING ENTEROCOLITIS

CROSS-REFERENCE TO RELATED APPLICATION

This application claims priority to U.S. Provisional Application Ser. No. 61/705,401 filed on Sep. 25, 2012, which is incorporated by reference herein in its entirety.

GRANT INFORMATION

This work was funded in part by Grant Number 1R01DK083752 from the National Institutes of Health. The United States Government has certain rights in the invention.

1. INTRODUCTION

The present invention relates to orally administered therapy to treat or reduce the risk of developing necrotizing enterocolitis in an infant.

2. BACKGROUND OF THE INVENTION

The leading cause of death from gastrointestinal disease in neonates is necrotizing enterocolitis ("NEC"; as reviewed in reference 51). 90 percent of the cases of NEC occur in premature infants (51). Over forty years of research have unfortunately made relatively little progress towards improving the prognosis of patients with NEC (3), which, after surgical treatment, bears a survival rate of only approximately 50% (4).

One area of recent development is the discovery that a class of bacterial receptors named Toll like receptors ("TLR's") play an essential role in the pathogenesis of NEC. Of particular importance is TLR4, the receptor for lipopolysaccharide (LPS), which is the outer membrane component of gram negative bacteria (12). It has been found that (i) mice with mutations in TLR4 are protected from the development of NEC (22); (ii) TLR4 signaling regulates the balance between injury and repair in the newborn intestine (21); and (iii) TLR4 is increased in the intestinal mucosa of mice, rats and humans with NEC compared to controls (21, 23). TLR4 activation appears to not only promote intestinal injury, but also reduces the ability of the mucosa to heal. It has been postulated that that prematurity, hypoxia and endotoxemia, each of which are linked to NEC, result in persistent upregulation of intestinal TLR4 and consequent disease (21). Therapeutic approaches to NEC have been developed that involve inhibiting activity of TLR4. For example, see U.S. Pat. No. 8,188,058 by Hackam.

Modulation of other TLRs may also be used therapeutically. Activation of TLR9, the enterocyte receptor for bacterial DNA (which, unlike mammalian DNA, is rich in CpG groups and significantly hypomethylated) with CpG-DNA led to reduced TLR4 signaling both in vitro and in newborn's intestine (U.S. Pat. No. 8,188,058 by Hackam and 40). The potential use of oral CpG-ODNs in asthma has been explored (53).

3. SUMMARY OF THE INVENTION

The present invention relates to methods of treating or reducing the risk of necrotizing enterocolitis (NEC) in an infant comprising orally administering an effective amount of a CpG-ODN. It is based, at least in part, on the results of experiments in which orally administered CpG-ODNs were observed to reduce the histopathology and markers of inflammation in a murine model for NEC. The present invention further provides for oral formulations of CpG-ODN for administration to infants.

4. BRIEF DESCRIPTION OF THE FIGURES

FIG. 1. Quantitative RT-PCR showing the effects of orally administered CpG-1 or CpG-2 on expression of tumor necrosis factor alpha ("TNRα") in the intestines of newborn mice which were either breast-fed controls ("BF") or treated by formula gavage and hypoxia to induce a murine model for NEC ("mNEC"). Measurements were made on day 4 after mNEC induction.

FIG. 2A-F. Representative hematoxylin and eosin ("H&E") stained histo-micrographs of the small intestine of newborn mice which were either BF controls or treated to produce mNEC. (A) Untreated BF control. (B) Untreated mNECI. (C) mNEC treated with CpG-1. (D) mNEC treated with CpG-2. (E) BF control treated with CpG-1. (F) BF control treated with CpG-2.

Figure 3:
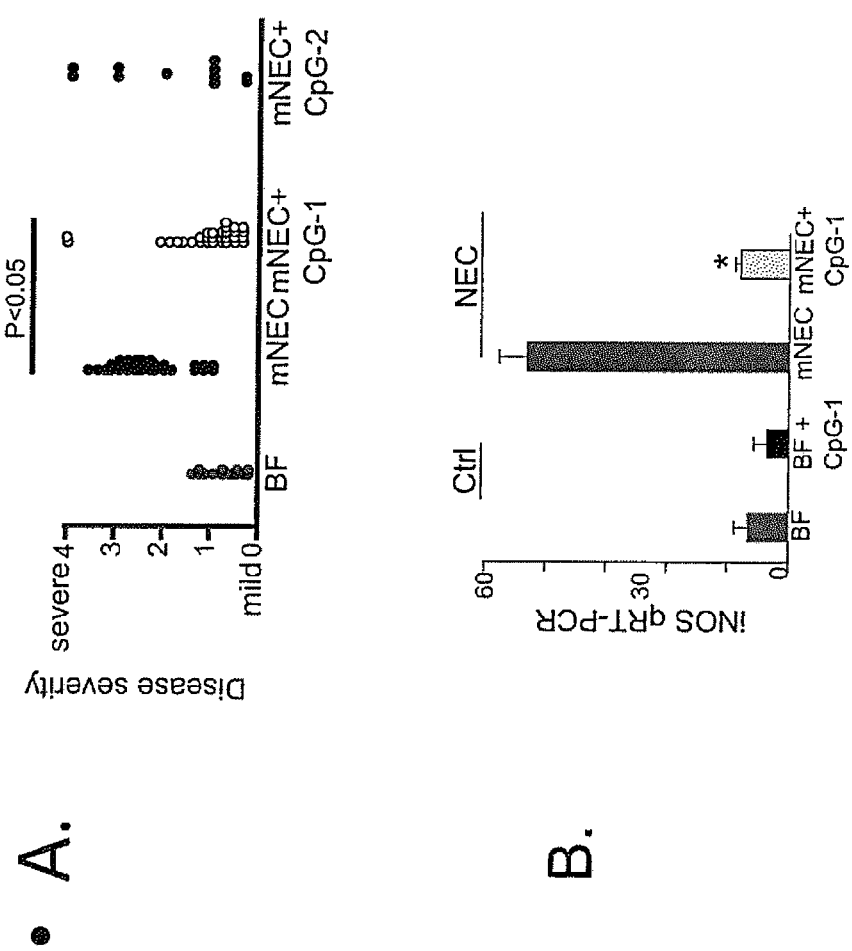

FIG. 3A-B. (A) Disease severity in BF controls or mNEC animals treated with either CpG-1 or CpG-2. Results for CpG-2 trended towards but did not reach statistical significance. (B) Inducible nitric oxide synthase (iNOS) as measured by qRT-PCR in BF controls or mNEC animals treated with CpG-1.

FIG. 4A-D. Confocal microscopy showing extent of NFκB activation in intestinal mucosa of newborn transgenic mice that express NFκB-GFP. Nuclei are indicated by areas of blue fluorescence. NFκB is detected by a red fluorescent anti-GFP antibody, and is more punctate. Newborn mice were either (A) BF controls treated with saline; (B) mNEC mice treated with saline; or (C) mNEC mice treated with CpG-2. (D) is graphical depiction of results, showing the relative red (GFP) pixel intensity for each animal.

Figure 5:

FIG. 5. Gross images of mice with mNEC that are untreated or have been treated with oral CpG-1 or CpG-2.

FIG. 6A-C. Effects of pre-treatment of mice prior to induction of NEC. (A) Mucosal iNOS expression (as measured by RT-PCR) in BF controls, untreated mNEC animals, mice pre-treated with CpG-1 for 48 hours prior to attempted induction of NEC ("mNEC Cpg1") and BF mice treated with CpG-1 for 48 hours. (B) Mucosal TNFα expression (as measured by RT-PCR) in BF controls, untreated mNEC animals, mice pre-treated with CpG-1 for 48 hours prior to attempted induction of NEC ("mNEC Cpg1") and BF mice treated with CpG-1 for 48 hours. (C) Weight at the time of euthanasia of BF controls, untreated mNEC animals, mice pre-treated with CpG-1 for 48 hours prior to attempted induction of NEC ("mNEC Cpg1") and BF mice treated with CpG-1 for 48 hours.

Figure 7:
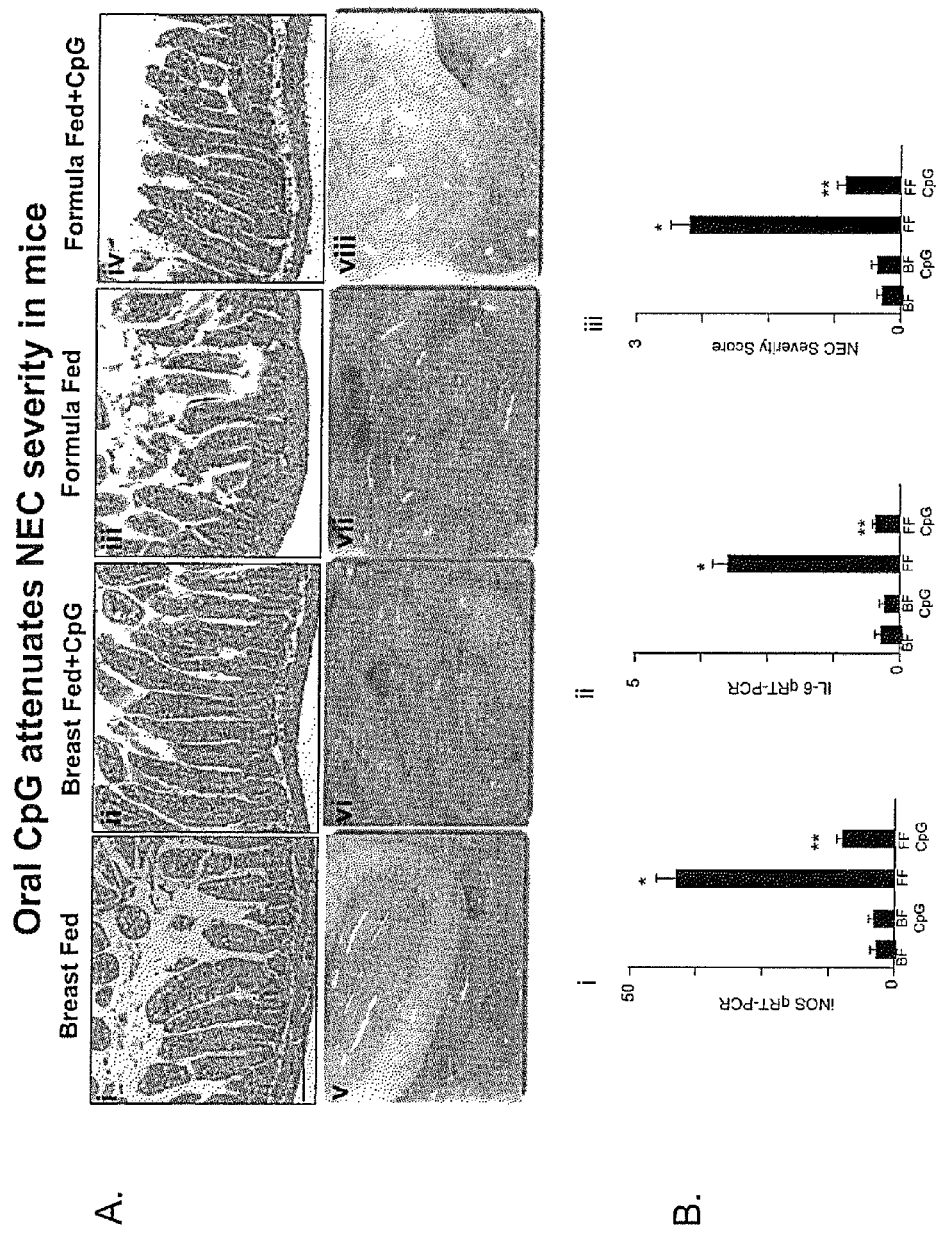

FIG. 7A-B. Oral CpG attenuates intestinal inflammation in experimental NEC. (A) Representative photomicrographs (i-iv) and gross images (v-viii) of the ileum from neonatal mice that were either breast fed (BF) (i, v), BF in the presence of CpG (ii, vi), induced to develop NEC by formula feeding (FF) along with vehicle (iii, vii), or induced to develop NEC by FF in the presence of oral CpG (1 mg/kg/day) (iv, viii). (B) qRT-PCR showing the expression of iNOS (i) and IL-6 (ii) in the intestinal mucosa and NEC severity score (iii) of newborn mice that were either breast fed (BF), BF in the presence of CpG, induced to develop NEC (FF), or induced to develop NEC (FF) in the presence of oral CpG (1 mg/kg). Size bar=10 μm. Shown are mean±SEM. *p<0.05

FF vs BF; **p<0.05 FF+CpG vs F F. Representative of 5 separate experiments with over 5 neonatal mice per group.

FIG. 8A-B. CpG inhibits TLR4-mediated inflammation in human ex vivo control and NEC intestinal tissue. (A) qRT-PCR showing expression of IL1β (i) and TLR4 (ii) in the resected Ileal tissue from neonates with healed NEC at the time of stoma closure that was pretreated with or without CpG for 30 minutes prior to subsequent LPS administration for 3 hours. (B) qRT-PCR showing expression of iNOS (i) and IL-6 (ii) in the resected Ileal tissue from neonates with NEC that was pretreated with or without CpG for 30 minutes prior to subsequent LPS administration for 3 hours. Shown is mean±SEM from 3 separate specimens; *p<0.05 LPS vs Control (Ctrl); **p<0.05 LPS vs LPS+CpG.

SEQUENCE LISTING

The specification further incorporates by reference the Sequence Listing submitted herewith via EFS on Sep. 25, 2013. Pursuant to 37 C.F.R. §1.52(e)(5), the Sequence Listing text file, identified as 0723960496US_ST25.txt, is 8,390 bytes and was created on Sep. 25, 2013. The Sequence Listing, electronically filed herewith, does not extend beyond the scope of the specification and thus does not contain new matter.

5. DETAILED DESCRIPTION OF THE INVENTION

For clarity of disclosure, and not by way of limitation, the detailed description of the invention is divided into the following subsections:
(i) CpG oligonucleotides;
(ii) CpG formulations;
(iii) methods of treating NEC; and
(iv) methods of reducing the risk of NEC.

5.1 CpG Oligonucleotides

CpG oligonucleotides, as that term is used herein, are oligonucleotides comprising one or more unmethylated CpG dinucleotide ("CpG ODNs").

In certain non-limited embodiments a CpG ODN is between about 7 and 200 nucleotides in length, or between about 10 and 100 nucleotides in length, or between about 10 and 50 bases nucleotides in length, or between about 10 and 30 nucleotides in length.

In some non-limiting embodiments, the CpG ODN is at least 6, or at least 7, or at least 8, or at least 9, or at least 10, or at least 11, or at least 12, or at least 13, or at least 14, or at least 15, or at least 16, or at least 17, or at least 18, or at least 19, or at least 20, or at least 21, or at least 22, or at least 23, or at least 24, or at least 25, or at least 26, or at least 27, or at least 28, or at least 29, or at least 30 nucleotides in length.

In some non-limiting embodiments, the CpG-ODN is up to about 25, up to about 30, up to about 35, up to about 40, up to about 45 or up to about 50 nucleotides in length.

In one non-limiting embodiment, the CpG ODN is about 15, about 16, about 17, about 18, about 19, about 20, about 21, about 22, about 23, about 24, about 25, about 26, about 27, about 28, about 29, about 30, about 31, about 32, about 33, about 34, or about 35 nucleotides in length.

In non-limiting embodiments of the invention, such oligonucleotides may contain one or more phosphorothioate linkages (at some or all bonds) or other modifications which improve stability, uptake, etc., (for example, but not limited to, a poly-G tail (for example, but not by way of limitation, of at least five or at least ten or at least 15 residues in length)). The CpG ODN may be double stranded, single stranded, or contain single and double-stranded regions (e.g., contain a hairpin). The CpG oligonucleotide may be DNA or RNA and may contain non-naturally occurring bases and/or linkages.

In certain non-limiting embodiments a CpG ODN may promote activation of TLR9 in vitro and/or in vivo. A number of CpG ODNs that activate TLR9 are known in the art. Some are species specific. Non-limiting examples follow.

Human CpG ODNs have been divided into three types, as follows:

Type A (D) CpG ODNs, which have polyG motifs with phosphohorothioate linkages at the 5' and 3' ends and a PO-containing palindrome CpG-containing motif at its center—these are strong inducers of IFN-alpha production by plasmacytoid dendritic cells and are potent NK cell activators;

Type B (K) CpG ODNs, which have a full phosphorothioate backbone with one or more CpG motifs without polyG; they are potent activators of B cells but weaker inducers of IFN-alpha production; and Type C CpG ODNs, which have a complete phosphorothioate backbone without polyG, but have CpG motifs and palindromes; they produce A and B-like effects (stimulate IFN-alpha and B cells).

Either type A, type B or type C human-selective CpG ODNs may be used according to the invention. Non-limiting example of CpG ODNs which are selectively active in humans and may be used according to the invention include, but are not limited to, 5'-TCG TCG TTT TGT COT TTT GTC GTT-3' (SEQ ID NO:1; CpG ODN 2006, InvivoGen, San Diego, Calif.), CpG ODN 2006-G5 (InvivoGen, San Diego, Calif.), 5'-GGG GGA CGA TCG TCG GGG GG-3' (SEQ ID NO:2; CpG ODN 2216, InvivoGen, San Diego, Calif.), 5'-TCG TCG TCG TTC GAA CGA CGT TGA T-3' (SEQ ID NO:3; CpG ODN M362, InvivoGen, San Diego, Calif.), 5'-TCG TCG TTT TGT CGT TTT GTC GTT-3' (SEQ ID NO:4; CpG ODN 7909, Coley Pharmaceutical Group, Ottawa, Ontario, Canada (Pfizer)), D(5'-TCT-GTCGTTCT-X-TCTTGCTGTCT-3') (SEQ ID NO:5) where X is a glycerol linker (Idera Pharmaceuticals, Cambridge, Mass.; see Putta et al., Nucl. Acids Res. 34(11):3231-3238), 5'-TCCATGACGTTCCTGACGTT-3' (SEQ ID NO:6; ODN 1826, preferably phosphorothioated), d(5'-TCTGTC*GTTCT-X-TCTTGC*TGTCT-3') (SEQ ID NO:7) where C*=$N^3$-Me-dC and X is a glycerol linker (Idera Pharmaceuticals, Cambridge, Mass.; see Putta et al., Nucl. Acids Res. 34(11):323'-3238), and d(5'-TCTGTCG*TTCT-X-TCTTG*CTGTCT-3') (SEQ ID NO:8) where G=$N^1$-Me-dG and X is a glycerol linker (Idera Pharmaceuticals, Cambridge, Mass.; see Putta et al., Nucl. Acids Res. 34(11):3231-3238).

In further embodiments, the present invention provides for the use of CpG ODNs which are at least 90 percent and preferably at least 95 percent homologous to any of the CpG ODNs referred to herein (where homology may be detetinined by standard software such as BLAST or PASTA).

In one particular, non-limiting embodiment, the CpG ODN, 5'-TCCATGACGTTCCTGACGTT-3' (SEQ ID NO:6), containing phosphorothioate linkages, known in the art as CpG ODN 1826 (Coley Pharmaceutical Group, Ottawa, Ontario, Canada (Pfizer)), which shows selective activation of murine TLR9, may be used. In addition, CpG ODNs which are at least about 90 percent, and preferably at least about 95 percent, homologous to CpG ODN 1826 may be used, where homology may be measured using a standard software program such as BLAST or FASTA. CpG ODN 1826 is referred to as CpG-1 in Example 6 below.

In yet another specific, non-limiting embodiment, the CpG-ODN 5'TCGTCGTTTTGTCGTTCCTGACGTT 3' (SEQ ID NO:9), referred to herein as CpG-2, may be used. In addition, CpG ODNs which are at least about 90 percent, and preferably at least about 95 percent, homologous to CpG 2 may be used, where homology may be measured using a standard software program such as BLAST or FASTA. In non-limiting embodiments of the invention, a mixture of two or more CpG ODNs may be used.

In some non-limiting embodiments, the CpG-ODN comprises the sequence 5' GTCGTT 3' (SEQ ID NO: 10).

In some non-limiting embodiments, the CpG-ODN comprises the sequence 5' GTCGTTT 3' (SEQ ID NO:11).

In some non-limiting embodiments, the CpG-ODN comprises the sequence 5' CGTCGTTT 3' (SEQ ID NO:12).

In some non-limiting embodiments, the CpG-ODN comprises the sequence 5' GTCGTTTT 3' (SEQ ID NO:13).

In some non-limiting embodiments, the CpG-ODN comprises the sequence 5' CGTCGTTTT 3' (SEQ ID NO:14).

In some non-limiting embodiments, the CpG-ODN comprises the sequence 5' GTCGTTTTGTC 3' (SEQ ID NO:15).

In some non-limiting embodiments, the CpG-ODN comprises the sequence 5' TCGTCGTTTTGTC 3' (SEQ ID NO:16).

In some non-limiting embodiments, the CpG-ODN comprises the sequence 5' GACGTT 3' (SEQ ID NO:17).

In some non-limiting embodiments, the CpG-ODN comprises the sequence 5' TGACGTT 3' (SEQ ID NO:18).

In some non-limiting embodiments, the CpG-ODN comprises the sequence 5' CTGACGTT 3' (SEQ ID NO:19).

In some non-limiting embodiments, the CpG-ODN comprises the sequence 5'TCCTGACGTT 3' (SEQ ID NO:20).

In some non-limiting embodiments, the CpG-ODN comprises one or more of SEQ ID NO:10, for example, one, two, three or four of SEQ ID NO:10.

In some non-limiting embodiments, the CpG-ODN comprises one or more copy of SEQ ID NO:10, 11, 12, 13, 14, 15, 16, or a combination thereof, for example, one, two, three or four copy or copies of SEQ ID NO:10, 11, 12, 13, 14, 15, 16, or a combination thereof.

In some non-limiting embodiments, the CpG-ODN comprises one or more copy of SEQ ID NO:10, for example, one, two, three or four copy or copies of SEQ ID NO:10, and also comprises one or more copy or copies of SEQ ID NO: 17, 18, 19, 20, or a combination thereof.

In some non-limiting embodiments, the CpG-ODN comprises one or more copy of SEQ ID NO:10, 11, 12, 13, 14, 15, 16, or a combination thereof, for example, one, two, three or four copy or copies of SEQ ID NO:10, and also comprises one or more copy or copies of SEQ ID NO: 17, 18, 19, 20, or a combination thereof. In some nonlimiting embodiments, the CpG-ODN comprises 5' GTCGTT 3' (SEQ ID NO:10) and 5' GACGTT 3' (SEQ ID NO:17).

For additional TLR9 agonists, see Daubenberger, 2007, Curr. Opin. Molec. Ther. 9:45-52 and Krieg, 2006, Nat. Rev. Drug Disc. 5:471-484.

The CpG-ODN may optionally be linked to a carrier compound which may or may not be a nucleic acid, for example, but not limited to, a transport peptide that facilitates cellular uptake. The CpG-ODN may optionally be complexed with one or more additional compound, such as a peptide, or comprised in a micelle or liposome, to facilitate uptake. In non-limiting embodiments, the present invention provides for methods of identifying a CpG-ODN which may be used according to the invention comprising identifying a molecule which is capable of binding to TLR9 under physiologic conditions and which, in an in vivo system, in the presence of a TLR4-activating amount of LPS, decreases one or more of the relative amount of phosphorylated p38, the relative amount of phosphorylated ERK, the relative translocation of NFκB into the nucleus, or the amount of IL-6 produced. In addition to identifying test agents suitable for TLR9 activation, such method may also be used to confirm the activity or optimize the dosage of any of the particular CpG ODNs listed herein.

5.2 CpG Formulations

The present invention provides for pharmaceutical and nutriceutical formulations of CpG-ODNs for oral administration to an infant.

In certain non-limiting embodiments, the formulation is in the form of a liquid, a powder, a capsule, a tablet, or an orally disintegrating tablet.

A CpG comprised in said formulation may be contained in a particle such as a micelle, liposome, microsphere or nanoparticle.

In certain embodiments, where the formulation is a liquid, said formulation may be a solution, an emulsion, or a suspension.

In certain embodiments, where the formulation is a liquid, the formulation comprises a pharmaceutically suitable liquid such as, but not limited to, water, saline, or an emulsion formed between an aqueous solution and an oil or other liquid that is not substantially miscible with water. In a specific non-limiting embodiment a liquid formulation may comprise a hydrophobic compound as well as an emulsifier. Specific non-limiting examples of compounds which may be incorporated into formulations of the invention include: one or more fatty acid such as linoleic acid and/or oleic acid (and/or other fatty acids), cholesterol, vitamin E, phospholipid, casein, whey, and soy protein (and/or other milk proteins derived from cow, pig or other animal), and oligosaccharides including milk oligosaccharides and other complex or simple sugars.

In certain non-limiting embodiments, a therapeutically or prophylactically effective amount of CpG-ODN, optionally comprised in a particle such as a micelle, liposome, microsphere or nanoparticle, may be comprised in an infant nutritional formula. In certain non-limiting embodiments, the CpG-ODN may be added to a known infant nutritional formula for example, but not limited to, Similac®, Enfamil® or Gerber® formulas. In specific non-limiting embodiments such formula may be Similac® Premature Infant Formula, Enfamil® Premature LIPIL, Similac® Premature Infant Formula, or Gerber® Good Start. In certain non-limiting embodiments, a solid (e.g. powder) or liquid composition comprising CpG-ODN, optionally comprised in a particle such as a micelle, liposome, microsphere or nanoparticle, may be added to a commercially available infant nutritional formula prior to administration. Alternatively, CpG-ODN may be comprised into an infant nutritional formula that has not hitherto been commercially available, where said infant nutritional formula further comprises one or more nutrients such as proteins, lipids, carbohydrates, electrolytes, and/or vitamins; in a specific non-limiting embodiment said formula may be nutritionally complete (suitable as a sole source of nutrition for a normal or premature infant). The infant nutritional formula may be, without limitation, a liquid or a powder for reconstitution with liquid.

In specific non-limiting embodiments where the formulation is a liquid, the concentration of CpG-ODN may be such that it provides a daily dose of between about 0.1-10 mg/kg, or a daily dose of between about 0.5-10 mg/kg, or a daily dose of between about 0.1-3 mg/kg, or a daily dose of between about 0.5-2 mg/kg, for example but not limited to a daily dose of about 1 mg/kg (all ranges recited herein include the recited limits), or a daily dose of 0.5 mg/kg, 0.6 mg/kg, 0.7 mg/kg, 0.8 mg/kg, 0.9 mg/kg, 1.1 mg/kg, 1.2 mg/kg, 1.3 mg/kg, 1.4 mg/kg, 1.5 mg/kg, 1.6 mg/kg, 1.7 mg/kg, 1.8 mg/kg, 1.9 mg/kg, or 2.0 mg/kg. In one specific non-limiting embodiment, where the liquid formulation, further, is an infant nutritional formula, the concentration of CpG-ODN may be such that it provides a daily dose of between about 0.1-10 mg/kg, or between about 0.5-10 mg/kg, or between about 0.1-3 mg/kg, or between about 0.5-2 mg/kg, for example but not limited to a daily dose of about 1 mg/kg, where the amount to be consumed by an infant per day may be between about 2 and 50 fluid ounces or between about 2 and 15 fluid ounces or between about 5 and 30 fluid ounces or between about 12 and 40 fluid ounces. In specific non-limiting embodiments, the concentration of CpG-ODN in an infant nutritional formula may be between about 0.005-5.0 mg/fluid ounce, or between about 0.005-1.0 mg/fluid ounce or between about 0.01-1.0 mg/fluid ounce.

In one specific non-limiting embodiment the CpG-ODN may be added to other components of the formulation shortly prior to use, for example within 24 hours or within 6 hours or within 2 hours or within 1 hour of use.

5.3 Methods of Treating NEC

The present invention provides for a method of treating NEC comprising orally administering, to an infant suffering from NEC, a therapeutically effective amount of a CpG-ODN. "Treatment" according to the invention includes, without limitation, (1) decreasing the level of one or more index of inflammation (e.g., inflammatory cytokines such as TNF-α, IL-6, IL-12p40, IL-113); (2) decreasing a clinical marker of inflammation, such as leukocyte count, fever, hypotension; and/or (3) reducing the risk of an adverse outcome, such as death, organ failure, hypoxia, or the need for surgery. "Treatment" does not necessarily mean that the condition being treated will be cured. A "therapeutically effective amount" achieves treatment. The CpG-ODN may be comprised in a CpG formulation as set forth above.

In certain non-limiting embodiments of the invention, a therapeutically effective daily dose is between about 0.1-10 mg/kg, or between about 0.1-3 mg/kg, or between about 0.5-2 mg/kg, for example about 1 mg/kg, or a daily dose of 0.5 mg/kg, 0.6 mg/kg, 0.7 mg/kg, 0.8 mg/kg, 0.9 mg/kg, 1.1 mg/kg, 1.2 mg/kg, 1.3 mg/kg, 1.4 mg/kg, 1.5 mg/kg, 1.6 mg/kg, 1.7 mg/kg, 1.8 mg/kg, 1.9 mg/kg, or 2.0 mg/kg, which may be administered as a single or divided dose. In certain non-limiting embodiments, the period of treatment may be at least 1 day, at least 2 days, at least 3 days, at least 4 days, at least 5 days, at least 6 days, at least 7 days, at least 8 days, at least 9 days, at least 10 days, at least 11 days, at least 12 days, at least 13 days, at least 14 days, or at least three weeks up to one month or up to three months or up to 6 months or up to one year.

5.4 Methods of Reducing the Risk of NEC

The present invention provides for a method of reducing the risk of developing NEC comprising orally administering, to an infant in need of such treatment, a prophylactically effective amount of a CpG-ODN. "Reducing the risk" does not necessarily mean that the infant being treated will not develop NEC. A "prophylactically effective amount" reduces the risk of NEC by at least about ⅕ or by at least about ⅓. Any infant may be eligible for such prophylactic treatment, and infants at higher risk for NEC as a result of premature birth or low birth rate may particularly benefit. The CpG-ODN may be comprised in a CpG formulation as set forth above.

In certain non-limiting embodiments of the invention, a prophylactically effective daily dose is between about 0.1-10 mg/kg, for example about 1 mg/kg or between about 0.1-3 mg/kg or between about 0.5-1 mg/kg, or between about 0.1-1 mg/kg, or 0.1-0.5 mg/kg, or less than 1 mg/kg, which may be administered as a single or divided dose. In certain non-limiting embodiments, the period of prophylaxis may be at least one week, at least two weeks, at least three weeks, at least one month, at least two months, at least three months, at least four months, at least five months or at least six months up to one year.

6. Example 1

A murine model for NEC ("mNEC") was produced in newborn mice by 4 days of hypoxia and formula gavage (52), which leads to the induction of iNOS, reduced enterocyte proliferation, and disruption of the ileal mucosa ("mNEC" mice) as compared to control mice that were allowed to breast feed ("BF" mice"). Specifically, mNEC was induced in 10-d-old mice (12) using formula gavage [Similac Advance infant formula (Abbott Nutrition):Esbilac canine milk replacer, 2:1] 50 μL/g body weight, five times per day for 4 d, and hypoxia (5% O2, 95% N2) administered for 10 min twice daily for 4 d using a hypoxia chamber (Billups-Rothenberg Inc.). CpG-1 was TCCATGACGTTC-CTGACGTT-3' (SEQ ID NO:6), containing phosphorothioate linkages, known in the art as CpG ODN 1826 (Coley Pharmaceutical Group, Ottawa, Ontario, Canada (Pfizer)). CpG-2 was 5' TCGTCGTTTTGTCGTTCCTGACGTT 3' (SEQ ID NO:9). CpG-1 or CpG-2 was administered at a dose of 1 mg/kg at a frequency of twice per day in the infant formula described above. Oral administration to breast-fed and NEC animals was achieved by gavage with a silastic foam tipped angiocatheter.

Figure 2:
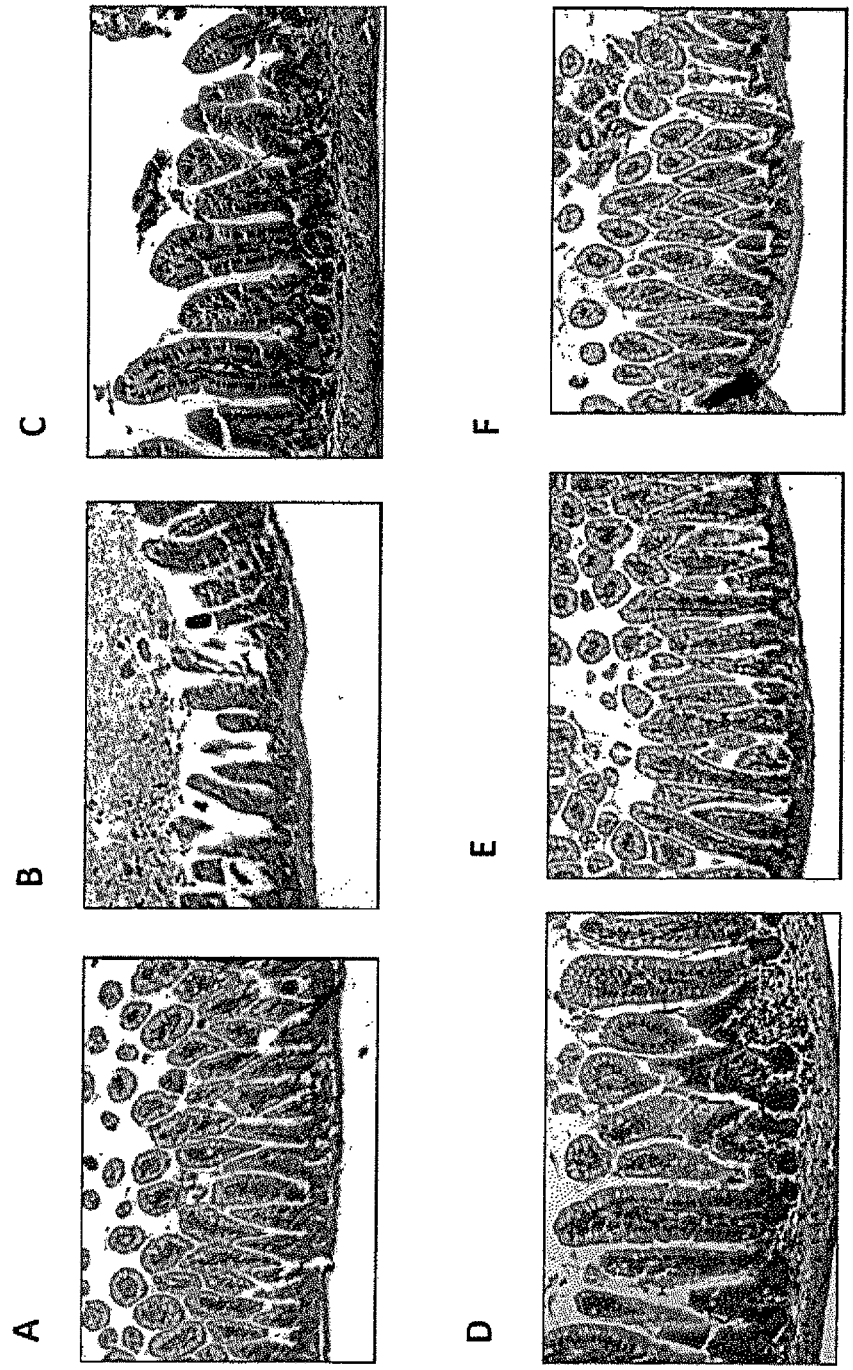

Quantitative RT-PCR was used to assess the effects of orally administered CpG-1 or CpG-2 on expression of the inflammatory cytokine tumor necrosis factor alpha (TNFα) in mNEC versus BF mice. Measurements were made on day 4 after mNEC induction. As shown in FIG. 1, oral administration of either CpG-1 or CpG-2 brought the levels of TNFα in mNEC animals down to approach the level in BF controls. Similarly, the elevated level of inducible nitric oxide synthase (iNOS) obseved in mNEC mice versus BF controls was substantially reduced by oral CpG (FIG. 3B). This effect was reflected by histologic evaluation, as depicted in FIG. 2A-F, where the disruption of the small intestine mucosa observed in untreated mNEC mice (FIG. 2B) is ameliorated in mNEC mice orally treated with CpG-1 or CpG-2 (FIGS. 2C and 2D, respectively) to resemble the mucosa of BF control (FIG. 2A).

Figure 4:
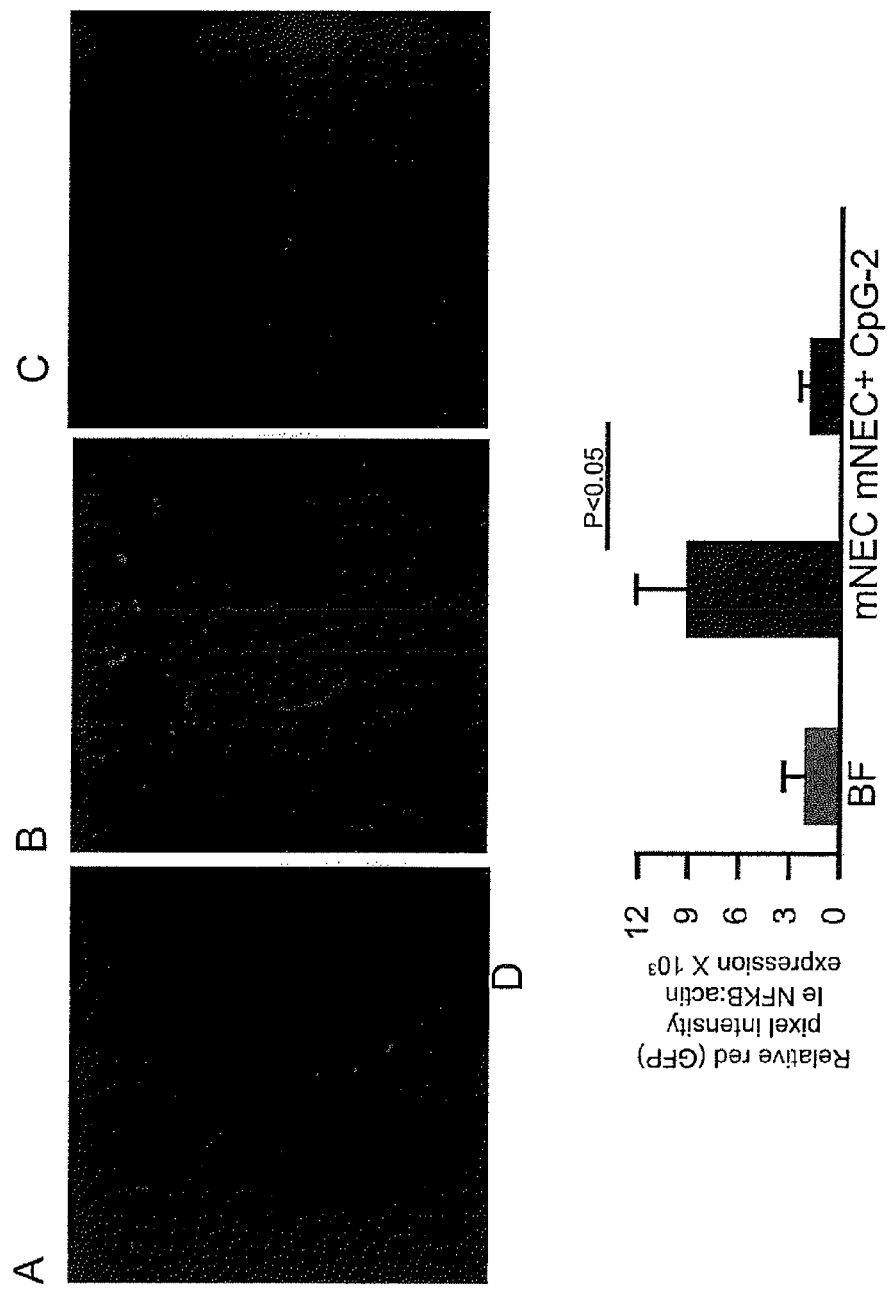

Consistent with these observations, oral CpG was found to decrease activation of NFκB, as indicated by localization of NFκB in the nucleus. As shown in FIG. 4A-C, confocal microscopy studies of BF or mNEC mice treated with saline (FIGS. 4A and 4B) showed nuclear localization of NFκB (punctate red fluorescence) in the saline-treated mNEC animals which was largely absent in mNEC mice treated with CpG-2 (FIG. 4C). A bar graph depiction of these results is shown in FIG. 4D. Further, the gross morphology of mNEC mice treated with oral CpG-1 or CpG-2 was much more robust than that of untreated mNEC mice (FIG. 5). This was reflected by a higher body weight in the treated animals.

Finally, it was shown that when CpG-1 was administered 48 hours prior to attempted induction of mNEC, mucosal expression of iNOS and TNFα were reduced almost to baseline levels and the weight of the pre-treated animals also approached controls (FIG. 6A-C). This data suggests that CpG-ODNs may be used to reduce the risk that an infant will develop NEC.

6. Example 2

The effect of CpG-ODN 5'-TCCATGACGTTCCT-GACGTT-3' (SEQ ID NO:6; ODN 1826) on inhibiting NEC in a murine NEC model in vivo, and in ex vivo human samples from infants undergoing intestinal resection for active NEC or at the time of stoma closure was examined. To determine the level of NEC inhibition, the extent of LPS signaling was determined by the degree of expression of pro-inflammatory cytokines iNOS and TNFα by Quantitative real-time PCR (qRT-PCR).

Materials and Methods
Induction of necrotizing enterocolitis in mouse model

All mice experiments were approved by the Institutional Animal Care and Use

Committee of the University of Pittsburgh. Swiss Webster mice were obtained from Charles River Laboratories. NEC was induced in 7-10 day old mice as described by Leaphart et al. (21) and Afrazi et al. (54) using formula gavage (a 2:1 ratio of Similac Advance infant formula (Ross Pediatrics): Esbilac canine milk replacer) administered five times/day, along with hypoxia (5% $O_2$, 95% $N_2$) for 10 min in a hypoxic chamber (Billups-Rothenberg, Inc., Del Mar, Calif.) twice daily, for 4 days. This protocol results in the development of patchy necrosis involving the small intestine, which is similar to human NEC, with an increase in circulating cytokines that mimics that observed in human NEC (40). CpG was administered via the oral route at a concentration of 1 mg/kg/day, which included 4 days of pretreatment prior to the start of the NEC model. Disease severity was determined on histological sections of the terminal ileum by a pediatric pathologist blinded to the study condition according to a scoring system from 0 (normal) to 3 (severe), as described by Leaphart et al. (21).

Human Necrotizing Enterocolitis

All human tissue was obtained and processed as discarded tissue via waiver of consent with approval from the University of Pittsburgh Institutional Review Board and in accordance with the University of Pittsburgh anatomical tissue procurement guidelines. Human tissue was obtained from infants undergoing intestinal resection for active NEC or at the time of stoma closure (healed NEC at the time of stoma closure). After initial review by the duty pathologist to ensure that adequate diagnostic information was obtained from the gross tissue specimen, the intestinal resection was divided into multiple pieces, and treated in triplicate with media alone, LPS 50 ug/ml, CpG (1 uM) alone or LPS+CpG as described by Neal et al. (55). After 3 hours of treatment, tissue was processed for qRT-PCR, and assessed for the expression of IL1β, TLR4, iNOS or IL-6.

RT-PCR

The extent of LPS signaling was determined by the degree of pro-inflammatory cytokines, iNOS, and TNFα by Quantitative real-time PCR (qRT-PCR). qRT-PCR was performed using the Bio-Rad CFX96 Real-Time System (Biorad, Hercules, Calif.) using the primers listed in the table below.

| Gene | Species | Forward sequence | Reverse sequence | Amplicon Size (bP) |
|---|---|---|---|---|
| iNOS | Mouse/Rat | CTGCTGGTGGTGACAA GCACATTT (SEQ ID NO: 21) | ATGTCATGAGCAAAGG CGCAGAAC (SEQ ID NO: 22) | 167 |
| | Human | AATGAGTCCCCGCAGC CCCT (SEQ ID NO: 23) | AGTCATCCCGCTGCCC CAGT (SEQ ID NO: 24) | 143 |
| RPLO | Mouse/Rat/ Human | GGCGACCTGGAAGTCC AACT (SEQ ID NO: 25) | CCATCAGCACCACAGC CTTC (SEQ ID NO: 26) | 143 |
| IL-6 | Mouse/Rat | GGCTAAGGACCAAGA CCATCCAA (SEQ ID NO: 27) | TCTGACCACAGTGAGG AATGTCCA (SEQ ID NO: 28) | 138 |
| | Human | TCTCCACAAGCGCCTT CG (SEQ ID NO: 29) | CTCAGGGCTGAGATGC CG (SEQ ID NO: 30) | 193 |
| IL1β | Human | AGTGTGGATCCCAAGC AATACCCA (SEQ ID NO: 31) | TGTCCTGACCACTGTT GTTTCCCA (SEQ ID NO: 32) | 175 |
| TLR4 | Human | AAGCCGAAAGGTGATT GTTG (SEQ ID NO: 33) | CTGAGCAGGGTCTTCT CCAC (SEQ ID NO: 34) | 153 |
| TNFa | Mouse/Rat | CATCTTCTCAAAATTC GAGTGACAA (SEQ ID NO: 35) | TGGGAGTAGACAAGGT ACAACCC (SEQ ID NO: 36) | 175 |
| | Human | GGCGTGGAGCTGAGA GATAAC (SEQ ID NO: 37) | GGTGTGGGTGAGGAGC ACAT (SEQ ID NO: 38) | 120 |

Statistical Analysis

Statistical analysis was performed using SPSS 13.0 software. ANOVA was used for comparisons for experiments involving more than two experimental groups. Two-tailed student's t-test was used for comparison for experiments consisting of two experimental groups. For analysis of the severity of NEC, chi-square analysis was performed.

Results

As shown in FIG. 7A, oral administration of CpG attenuates intestinal inflammation in experimental NEC induced in mouse through formula feeding. Additionally, oral administration of CpG to the mice with NEC induced through formula feeding reduced the expression of iNOS and IL-6 in the intestinal mucosa, and reduced the NEC severity score (FIG. 7B).

Figure 8:
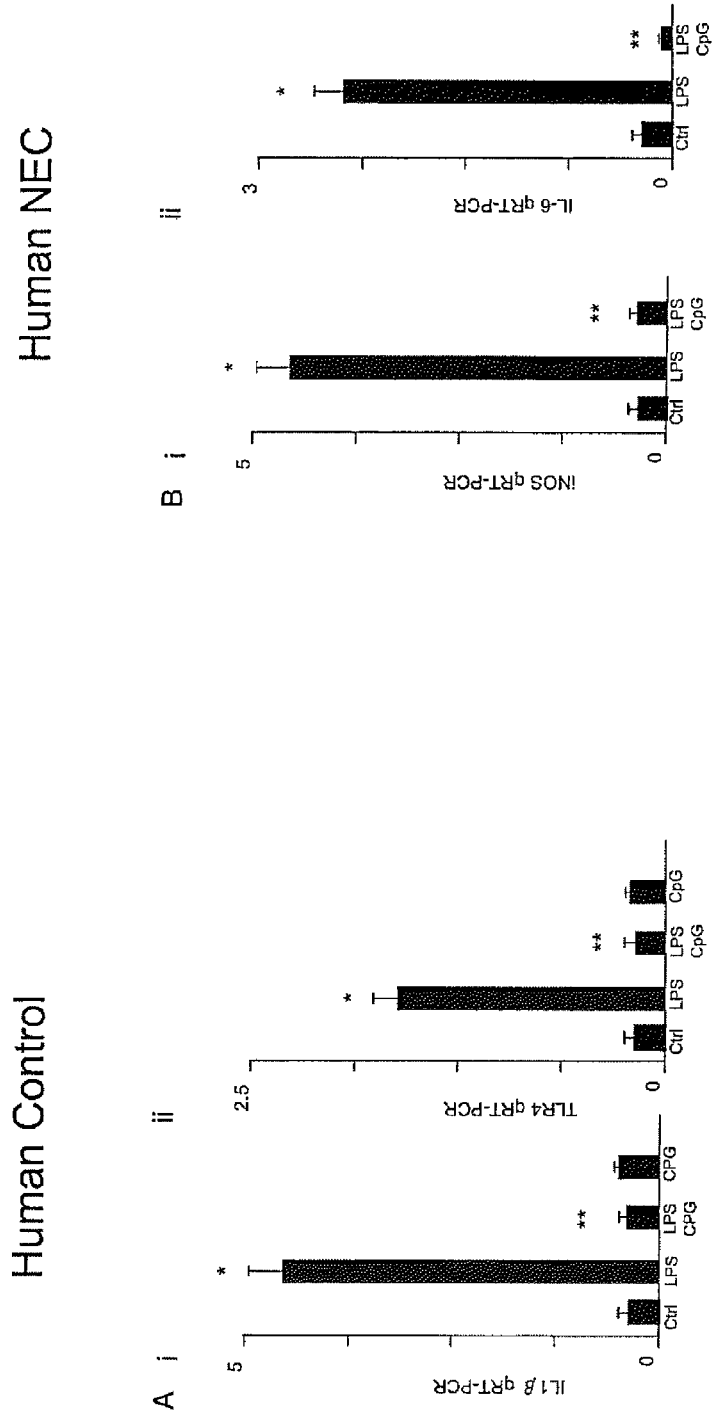

As shown in FIG. 8, CpG treatment inhibited TLR4-mediated inflammation in human ex vivo control and NEC intestinal tissue. As shown in FIG. 8A, the increase in expression of IL1β and TLR4 caused by LPS treatment in control tissue was reduced when CpG was also administered to the tissue. Similarly, in human NEC tissue, LPS treatment increased iNOS and IL-6 expression. However, when CpG was added to the treatment, the expression of the Expression of iNOS and IL-6 was reduced.

7. REFERENCES

1. Luig M, Lui K. Epidemiology of necrotizing enterocolitis—Part I: Changing regional trends in extremely preterm infants over 14 years. J Paediatr Child Health. 2005; 41:169-173.
2. Gagliardi L, Bellu R, Cardilli V, De Curtis M. Necrotising enterocolitis in very low birth weight infants in Italy: incidence and non-nutritional risk factors. J Pediatr Gastroenterol Nutr. 2008; 47:206-210.
3. Mizrahi A, Barlow O, Berdon W, Blanc W A, Silverman W A. Necrotizing enterocolitis in premature infants. J. Pediatr. 1965; 66:697-705.
4. Blakely M L, Lally K P, McDonald S, Brown R L, Barnhart D C, Ricketts R R, Thompson W R, Scherer L R, Klein M D, Letton R W, Chwals W I, Touloukian R J, Kurkchubasche A G, Skinner M A, Moss R L, Hilfiker M L. Network NECSotNNR. Postoperative outcomes of extremely low birth-weight infants with necrotizing enterocolitis or isolated intestinal perforation: a prospective cohort study by the NICHD Neonatal Research Network. Ann Surg. 2005; 241:984-989. discussion 989-994.
5. Lin H C, Su B H, Chen A C, Lin T W, Tsai C H, Yeh T F, Oh W. Oral probiotics reduce the incidence and severity of necrotizing enterocolitis in very low birth weight infants. Pediatrics. 2005; 115:1-4.
6. Grave G D, Nelson S A, Walker W A, Moss R L, Dvorak B, Hamilton F A, Higgins R, Raju T N. New therapies and preventive approaches for necrotizing enterocolitis: report of a research planning workshop. Pediatr Res. 2007; 62:510-514.
7. Iwasaki A, Medzhitov R. Regulation of adaptive immunity by the innate immune system. Science. 2010; 327: 291-295.
8. Wynn J, Cornell T T, Wong H R, Shanley T P, Wheeler D S. The host response to sepsis and developmental impact. Pediatrics. 2010; 125:1031-1041.
9. Medzhitov R, Preston-Hurlburt P, Janeway C A., Jr A human homologue of the Drosophila Toll protein signals activation of adaptive immunity. Nature. 1997; 388:394-397.
10. Lemaitre B, Nicolas E. Michaut L, Reichhart J M, Hoffmann J A. The dorsoventral regulatory gene cassette spatzle/Toll/cactus controls the potent antifungal response in Drosophila adults. Cell. 1996; 86:973-983.
11. Roach J C, Glusman G, Rowen L, Kaur A, Purcell M K, Smith K D, Hood L E, Aderem A. The evolution of vertebrate Toll-like receptors. Proc Natl Acad Sci USA. 2005; 102:9577-9582.
12. Poltorak A, He X, Smirnova I, Liu M Y, Van Huffel C, Du X, Birdwell D, Alejos E, Silva M, Galanos C, Freudenberg M, Ricciardi-Castagnoli P, Layton B, Beutler B. Defective LPS signaling in C3H/HeJ and C57BL/10ScCr mice: mutations in Tlr4 gene. Science. 1998; 282:2085-2088.
13. Hotta T, Yoshida N, Yoshikawa T, Sugino S, Kondo M. Lipopolysaccharide-induced colitis in rabbits. Res Exp Med (Berl) 1986; 186:61-69.
14. Feng J, El-Assal O N, Besner G E. Heparin-binding EGF-like growth factor (HB-EGF) and necrotizing enterocolitis. Semin Pediatr Surg. 2005; 14:167-174.
15. Feng J, Besner G E. Heparin-binding epidermal growth factor-like growth factor promotes enterocyte migration and proliferation in neonatal rats with necrotizing enterocolitis. J Pediatr Surg. 2007; 42:214-220.
16. Kruis W, Schussler P, Weinzierl M, Galanos C, Eisenburg J. Circulating lipid A antibodies despite absence of systemic endotoxemia in patients with Crohn's disease. Dig Dis Sci. 1984; 29:502-507.
17. Caradonna L, Amati L, Lella P, Jirillo E, Caccavo D. Phagocytosis, killing, lymphocyte-mediated antibacterial activity, serum autoantibodies, and plasma endotoxins in inflammatory bowel disease. Am J. Gastroenterol. 2000; 95:1495-1502.
18. Noerr B. Current controversies in the understanding of necrotizing enterocolitis. Adv Neonatal Care. 2003; 3; 107-120.
19. Sharma R, Tepas J J, 3rd, Hudak M L, Mollitt D L, Wludyka P S, Teng R J, Premachandra B R. Neonatal gut barrier and multiple organ failure: role of endotoxin and proinflammatory cytokines in sepsis and necrotizing enterocolitis. J Pediatr Surg. 2007; 42:454-461.
20. Duffy L C, Zielezny M A, Carrion V, Griffiths E, Dryja D, Hilty M, Rook C, Morin F., 3rd Concordance of bacterial cultures with endotoxin and interleukin-6 in necrotizing enterocolitis. Dig Dis Sci. 1997; 42:359-365.
21. Leaphart C L, Cavallo J C, Gribar S C, Cetin S, Li J, Branca M F, Dubowski T D, Sodhi C P, Hackam D J. A critical role for TLR4 in the pathogenesis of necrotizing enterocolitis by modulating intestinal injury and repair. J. Immunol. 2007; 179:4808-4820.
22. Jilling T, Simon D, Lu J, Meng F J, Li D, Schy R, Thomson R B, Soliman A, Arditi M, Caplan M S. The roles of bacteria and TLR4 in rat and murine models of necrotizing enterocolitis. J. Immunol. 2006; 177:3273-3282.
23. Chan K L, Wong K F, Luk J M. Role of LPS/CD14/TLR4-mediated inflammation in necrotizing enterocolitis: pathogenesis and therapeutic implications. World J. Gastroenterol. 2009; 15:4745-4752.
24. Richardson W M, Sodhi C P, Russo A, Siggers R H, Afrazi A, Gribar S C, Neal M D, Dai S, Prindle T J, Branca M, Ma C, Ozolek J, Hackam D J. Nucleotide-binding oligomerization domain-2 inhibits toll like receptor-4 signaling in the intestinal epithelium. Gastroenterology. 2010; 139:904-917.
25. Sodhi C P, Shi X H, Richardson W M, Grant Z S, Shapiro R A, Prindle T J, Branca M, Russo A, Gribar S C, Ma C. Hackam D J. Toll-like receptor-4 inhibits enterocyte proliferation via impaired beta-catenin signaling in necrotizing enterocolitis. Gastroenterology. 2010; 138:185-196.

26. Qureshi F G, Leaphart C, Cetin S, Li J, Grishin A, Watkins S, Ford H R, Hackam D J. Increased expression and function of integrins in enterocytes by endotoxin impairs epithelial restitution. Gastroenterology. 2005; 128:1012-1022.

27. Wolfs T G, Derikx J P, C. M. H, Vanderlocht J, Driessen A, de Bruïne A P, Bevins C L, Lasitschka F, Gassier N, van Gernert W G, Buurman W A. Localization of the lipopolysaccharide recognition complex in the human healthy and inflamed premature and adult gut. Inflamm Bowel Dis. 2010; 16:68-75.

28. Liu Y, Zhu L, Fatheree N Y, Liu X, Pacheco S E, Tatevian N, Rhoads J M. Changes in intestinal toll-like receptors and cytokines precede histological injury in a rat model of necrotizing enterocolitis. Am J Physiol Gastrointest Liver Physiol. 2009; 297:G442-G450.

29. Lu J, Jilling T, Li D, Caplan M S. Polyunsaturated fatty acid supplementation alters proinflammatory gene expression and reduces the incidence of necrotizing enterocolitis in a neonatal rat model. Pediatr Res. 2007; 61:427-432

30. Cetin S, Ford H R, Sysko L R, Agarwal C, Wang J, Neal M D, Baty C, Apodaca G, Hackam D J. Endotoxin inhibits intestinal epithelial restitution through activation of Rho-GTPase and increased focal adhesions. J Biol Chem. 2004; 279:24592-24600.

31. Dai S, Sodhi C P, Cetin S, Richardson W, Branca M, Neal M D, Prindle T, Ma C, Shapiro R A, Li B, Wang J H, Hackam D J. Extracellular high mobility group box1 (HMGB1) inhibits enterocyte migration via activation of toll like receptor 4 and increased cell-matrix adhesiveness. J Biol Chem. 2010; 285:4995-5002.

32. Zheng L, Riehl T E, Stenson W F. Regulation of colonic epithelial repair in mice by Toll-like receptors and hyaluronic acid. Gastroenterology. 2009; 137:2041-2051.

33. Fukata M, Chen A, Klepper A, Krishnareddy S, Vamadevan A S, Thomas L S, Xu R, Inoue H, Arditi M, Dannenberg A J, Abreu M T. Cox-2 is regulated by Toll-like receptor-4 (TLR4) signaling: Role in proliferation and apoptosis in the intestine. Gastroenterology. 2006; 131:862-877.

34. Fukata M, Michelsen K S, Fri R, Thomas L S. Hu B, Lukasek K, Nast C C, Lechago J, Xu. R, Naiki Y, Soliman A, Arditi M, Abreu M T. Toll-like receptor-4 is required for intestinal response to epithelial injury and limiting bacterial translocation in a murine model of acute colitis. Am J Physiol Gastrointest Liver Physiol. 2005; 288: G1055-G1065.

35. Rakoff-Nahoum S, Paglino J, Eslami-Varzaneh F, Edberg S, Medzhitov R. Recognition of commensal microflora by toll-like receptors is required for intestinal homeostasis. Cell. 2004; 118:229-241.

36. Fukata M, Hernandez Y, Conduah D, Cohen J, Chen A, Breglio K, Goo T, Hsu D, Xu R, Abreu M T. Innate immune signaling by Toll-like receptor-4 (TLR4) shapes the inflammatory microenvironment in colitis-associated tumors. Inflamm Bowel Dis. 2009; 15:997-1006

37. Lotz M, Gutle D, Walther S, Menard S, Bogdan C, Hornef M W. Postnatal acquisition of endotoxin tolerance in intestinal epithelial cells. J Exp Med. 2006; 203:973-984.

38. Wang J, Ford H R, Grishin A V. NF-kappaB-mediated expression of MAPK phosphatase-1 is an early step in desensitization to TLR ligands in enterocytes. Mucosal Immunol. 2010; 3:523-534.

39. Wang J, Ouyang Y, Guner Y, Ford H R, Grishin A V. Ubiquitin-editing enzyme A20 promotes tolerance to lipopolysaccharide in enterocytes. J. Immunol. 2009; 183: 1384-1392.

40. Gribar S C, Sodhi C P, Richardson W M, Anand. R J, Gittes G K, Branca M F, Jakub A, Shi X H, Shah S, Ozolek J A, Hackam D J. Reciprocal expression and signaling of TLR4 and TLR9 in the pathogenesis and treatment of necrotizing enterocolitis. J. Immunol. 2009; 182:636-646.

41. Borzutzky A, Fried A, Chou J, Bonilla F A, Kim S, Dedeoglu P. NOD2-associated diseases: Bridging innate immunity and autoinflammation. Clin Immunol. 2010; 134:251-261.

42. Milla P J, Fenton T R. Small intestinal motility patterns in the perinatal period. J Pediatr Gastroenterol Nutr. 1983; 2:S141-S144.

43. Shindou H, Ishii N, Uozumi T, Shimizu T. Roles of cytosolic phospholipase A2 and platelet-activating factor receptor in the Ca-induced biosynthesis of PAF. Biochem Biophys Res Commun. 2000; 271:812-817.

44. Svetlov S I, Liu H, Chao W, Olson M S. Regulation of platelet-activating factor (PAF) biosynthesis via coenzyme A-independent transacylase in the macrophage cell line IC-21 stimulated with lipopolysaccharide. Biochim Biophys Acta. 1997; 1346:120-130.

45. Izumi T, Shimizu T. Platelet-activating factor receptor: gene expression and signal transduction. Biochim Biophys Acta. 1995; 1259:317-333.

46. Muguruma K, Gray P W, Tjoelker L W, Johnston J M. The central role of PAF in necrotizing enterocolitis development. Adv Exp Med Biol. 1997; 407:379-382.

47. Amer M D, Hedlund E, Rochester J, Caplan M S. Platelet-activating factor concentration in the stool of human newborns: effects of enteral feeding and neonatal necrotizing enterocolitis. Biol Neonate. 2004; 85:159-166.

48. Caplan M S, Hedlund E, Adler L, Lickerman M, Hsuce W. The platelet activating factor receptor antagonist WEB 2170 prevents neonatal necrotizing enterocolitis in rats. J Pediatr Gastroenterol Nutr. 1997; 24:296-301.

49. Caplan M S, Lickerman M, Adler L, Dietsch G N, Yu A. The role of recombinant platelet activating factor acetylhydrolase in a neonatal rat model of necrotizing enterocolitis. Pediatr Res, 1997; 42:779-783.

50. Worthen G S, Seccombe J F, Clay K L, Guthrie L A, Johnston R B., Jr The priming of neutrophils by lipopolysaccharide for production of intracellular platelet-activating factor: potential role in mediation of enhanced superoxide secretion. J. Immunol. 1988; 140:3553-3559.

51. Afrazi A, et al. (2011) New insights into the pathogenesis and treatment of necrotizing enterocolitis: Toll-like receptors and beyond. Pediatr Res 69:183-188.

52. Richardson W M, et al. (2010) Nucleotide-binding oligomerization domain-2 inhibits toll-like receptor-4 signaling in the intestinal epithelium. Gastroenterology 139: 904-917, 917, e1-e6.

53. Kitagaki, K et al., (2006) Oral administration of CpG-ODNs suppresses antigen-induced asthma in mice. Clin Exp Immunol. 143(2): 249-259.

54. Afrazi A, Sodhi C P, Good M, et al. Intracellular Heat Shock Protein-70 Negatively Regulates TLR4 Signaling in the Newborn Intestinal Epithelium. J Immunol 2012; 188:4543-57.

55. Neal M D, Sodhi C P, Dyer M, et al. A Critical Role for TLR4 Induction of Autophagy in the Regulation of Enterocyte Migration and the Pathogenesis of Neerotizing Enterocolitis. J Immunol 2013.

Various publications are cited herein, the contents of which are hereby incorporated by reference in their entireties.

What is claimed is:

1. An infant nutritional formula comprising a therapeutically effective amount of a CpG-ODN comprising 5' TCGTCGTTTTGTCGTTCCTGACGTT 3' (SEQ ID NO:9), further comprising nutrients selected from the group consisting of proteins, lipids, carbohydrates, electrolytes, and vitamins.

2. The infant nutritional formula of claim 1, where the formula is nutritionally complete.

3. The infant nutritional formula of claim 1, where the concentration of CpG-ODN provides a daily dose of between about 0.1-10 mg/kg.

4. The infant nutritional formula of claim 3 where the daily dose provided is about 1 mg/kg.

5. The infant nutritional formula of claim 1, where the CpG-ODN is comprised in a particle selected from the group consisting of a micelle, liposome, microsphere or nanoparticle.

6. The infant nutritional formula of claim 1, wherein the CpG-ODN comprises one or more phosphorothioate linkage.

* * * * *

UNITED STATES PATENT AND TRADEMARK OFFICE
CERTIFICATE OF CORRECTION

PATENT NO. : 9,562,066 B2
APPLICATION NO. : 14/036960
DATED : February 7, 2017
INVENTOR(S) : David J. Hackam It is certified that error appears in the above-identified patent and that said Letters Patent is hereby corrected as shown below:

In the Specification

Please correct the paragraph in Column 1, Lines 11-16 as follows:
--STATEMENT OF GOVERNMENT INTEREST
This invention was made with government support under grant number DK083752 awarded by the National Institutes of Health. The government has certain rights in the invention.--

Signed and Sealed this
Twenty-fifth Day of June, 2019

Andrei Iancu
*Director of the United States Patent and Trademark Office*

SEQUENCE LISTING

<160> NUMBER OF SEQ ID NOS: 38

<210> SEQ ID NO 1
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 1
tcgtcgtttt gtcgttttgt cgtt                                                24

<210> SEQ ID NO 2
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 2 ggggga cgat cgtcggggggg                                                    20

<210> SEQ ID NO 3
<211> LENGTH: 25
<212> TYPE: DNA
<213> ORGANISM: Artificial sequence
<220> FEATURE:
<223> OTHER INFORMATION: Synthetic oligonucleotide

<400> SEQUENCE: 3
tcgtcgtcgt tcgaacgacg ttgat                                               25

<210> SEQ ID NO 4
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 4
tcgtcgtttt gtcgttttgt cgtt                                                24

<210> SEQ ID NO 5
<211> LENGTH: 22
<212> TYPE: DNA
<213> ORGANISM: Artificial sequence
<220> FEATURE:
<223> OTHER INFORMATION: Synthetic oligonucleotie
<220> FEATURE:
<221> NAME/KEY: misc_feature
<222> LOCATION: (11)..(12)
<223> OTHER INFORMATION: Glycerol linker between nucleotides 11 and 12.

<400> SEQUENCE: 5
tctgtcgttc ttcttgctgt ct                                                  22

<210> SEQ ID NO 6
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 6
tccatgacgt tcctgacgtt                                                     20

```
<210> SEQ ID NO 7
<211> LENGTH: 22
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (6)..()
<223> OTHER INFORMATION: C is N3-Me-dC
<220> FEATURE:
<221> NAME/KEY: misc_feature
<222> LOCATION: (11)..(12)
<223> OTHER INFORMATION: Glycerol linker between nucleotides 11 and 12.
<220> FEATURE:
<221> NAME/KEY: misc_feature
<222> LOCATION: (17)..()
<223> OTHER INFORMATION: C is N3-Me-dC

<400> SEQUENCE: 7
tctgtcgttc ttcttgctgt ct                                              22

<210> SEQ ID NO 8
<211> LENGTH: 22
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (7)..()
<223> OTHER INFORMATION: G is N1-Me-dG
<220> FEATURE:
<221> NAME/KEY: misc_feature
<222> LOCATION: (11)..(12)
<223> OTHER INFORMATION: Glycerol linker between nucleotides 11 and 12.
<220> FEATURE:
<221> NAME/KEY: misc_feature
<222> LOCATION: (16)..()
<223> OTHER INFORMATION: G is N1-Me-dG

<400> SEQUENCE: 8
tctgtcgttc ttcttgctgt ct                                              22

<210> SEQ ID NO 9
<211> LENGTH: 25
<212> TYPE: DNA
<213> ORGANISM: Artificial sequence
<220> FEATURE:
<223> OTHER INFORMATION: Synthetic oligonucleotide

<400> SEQUENCE: 9
tcgtcgtttt gtcgttcctg acgtt                                           25

<210> SEQ ID NO 10
<211> LENGTH: 6
<212> TYPE: DNA
<213> ORGANISM: Artificial sequence
<220> FEATURE:
<223> OTHER INFORMATION: Synthetic oligonucceotide

<400> SEQUENCE: 10 gtcgtt                                                                6

<210> SEQ ID NO 11
<211> LENGTH: 7
<212> TYPE: DNA
<213> ORGANISM: Artificial sequence
<220> FEATURE:
<223> OTHER INFORMATION: Synthetic oligonucleotide
```

```
<400> SEQUENCE: 11 gtcgttt                                                              7

<210> SEQ ID NO 12
<211> LENGTH: 8
<212> TYPE: DNA
<213> ORGANISM: Artificial sequence
<220> FEATURE:
<223> OTHER INFORMATION: Synthetic oligonucleotide

<400> SEQUENCE: 12 cgtcgttt                                                             8

<210> SEQ ID NO 13
<211> LENGTH: 8
<212> TYPE: DNA
<213> ORGANISM: Artificial sequence
<220> FEATURE:
<223> OTHER INFORMATION: Synthetic oligonucleotide

<400> SEQUENCE: 13 gtcgtttt                                                             8

<210> SEQ ID NO 14
<211> LENGTH: 9
<212> TYPE: DNA
<213> ORGANISM: Artificial sequence
<220> FEATURE:
<223> OTHER INFORMATION: Synthetic oligonucleotide

<400> SEQUENCE: 14 cgtcgtttt                                                            9

<210> SEQ ID NO 15
<211> LENGTH: 11
<212> TYPE: DNA
<213> ORGANISM: Artificial sequence
<220> FEATURE:
<223> OTHER INFORMATION: Synthetic oligonucleotide

<400> SEQUENCE: 15
gtcgttttgt c                                                        11

<210> SEQ ID NO 16
<211> LENGTH: 13
<212> TYPE: DNA
<213> ORGANISM: Artificial sequence
<220> FEATURE:
<223> OTHER INFORMATION: Synthetic oligonucleotide

<400> SEQUENCE: 16
tcgtcgtttt gtc                                                      13

<210> SEQ ID NO 17
<211> LENGTH: 6
<212> TYPE: DNA
<213> ORGANISM: Artificial sequence
<220> FEATURE:
<223> OTHER INFORMATION: Synthetic oligonucleotide

<400> SEQUENCE: 17 gacgtt                                                               6

<210> SEQ ID NO 18
<211> LENGTH: 7
```

```
<212> TYPE: DNA
<213> ORGANISM: Artificial sequence
<220> FEATURE:
<223> OTHER INFORMATION: Syntehtic oligonucleotide

<400> SEQUENCE: 18 tgacgtt                                                                    7

<210> SEQ ID NO 19
<211> LENGTH: 8
<212> TYPE: DNA
<213> ORGANISM: Artificial sequence
<220> FEATURE:
<223> OTHER INFORMATION: Synthetic oligonucleotide

<400> SEQUENCE: 19 ctgacgtt                                                                   8

<210> SEQ ID NO 20
<211> LENGTH: 10
<212> TYPE: DNA
<213> ORGANISM: Artificial sequence
<220> FEATURE:
<223> OTHER INFORMATION: Synthetic oligonucleotide

<400> SEQUENCE: 20
tcctgacgtt                                                                10

<210> SEQ ID NO 21
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 21
ctgctggtgg tgacaagcac attt                                                24

<210> SEQ ID NO 22
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 22
atgtcatgag caaaggcgca gaac                                                24

<210> SEQ ID NO 23
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 23
aatgagtccc cgcagcccct                                                     20

<210> SEQ ID NO 24
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 24
```
agtcatcccg ctgccccagt                                                     20

<210> SEQ ID NO 25
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 25
ggcgacctgg aagtccaact                                                     20

<210> SEQ ID NO 26
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 26
ccatcagcac cacagccttc                                                     20

<210> SEQ ID NO 27
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 27
ggctaaggac caagaccatc caa                                                 23

<210> SEQ ID NO 28
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 28
tctgaccaca gtgaggaatg tcca                                                24

<210> SEQ ID NO 29
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 29
tctccacaag cgccttcg                                                       18

<210> SEQ ID NO 30
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 30
ctcagggctg agatgccg                                                       18

<210> SEQ ID NO 31
<211> LENGTH: 24
<212> TYPE: DNA
<213> ORGANISM: Artificial sequence

```
<220> FEATURE:
<223> OTHER INFORMATION: Synthetic oligonucleotide

<400> SEQUENCE: 31
agtgtggatc ccaagcaata ccca                                              24

<210> SEQ ID NO 32
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 32
tgtcctgacc actgttgttt ccca                                              24

<210> SEQ ID NO 33
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 33
aagccgaaag gtgattgttg                                                   20

<210> SEQ ID NO 34
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 34
ctgagcaggg tcttctccac                                                   20

<210> SEQ ID NO 35
<211> LENGTH: 25
<212> TYPE: DNA
<213> ORGANISM: Artificial sequence
<220> FEATURE:
<223> OTHER INFORMATION: Synthetic oligonucleotide

<400> SEQUENCE: 35
catcttctca aaattcgagt gacaa                                             25

<210> SEQ ID NO 36
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 36
tgggagtaga caaggtacaa ccc                                               23

<210> SEQ ID NO 37
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 37
ggcgtggagc tgagagataa c                                                 21
```

```
<210> SEQ ID NO 38
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 38
ggtgtgggtg aggagcacat                                              20
```